United States Patent
Gong et al.

(10) Patent No.: US 6,825,026 B2
(45) Date of Patent: Nov. 30, 2004

(54) ISOLATED NUCLEIC ACID MOLECULES ENCODING HUMAN SYNTHASE PROTEINS, AND USES THEREOF

(75) Inventors: Fangcheng Gong, Germantown, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

(*) Notice: Subject to any disclaimer, the term of this patent is extended or adjusted under 35 U.S.C. 154(b) by 0 days.

(21) Appl. No.: 10/622,516

(22) Filed: Jul. 21, 2003

(65) Prior Publication Data

US 2004/0018545 A1 Jan. 29, 2004

Related U.S. Application Data

(62) Division of application No. 10/193,295, filed on Jul. 12, 2002, now Pat. No. 6,620,608, which is a division of application No. 09/819,993, filed on Mar. 29, 2001, now Pat. No. 6,436,692.

(51) Int. Cl.$^7$ .......................... C12N 9/88; C12N 15/00; C12N 5/00; C12N 1/20; C07H 21/04
(52) U.S. Cl. ................. 435/232; 435/320.1; 435/252.3; 435/325; 435/69.1; 536/23.2; 530/350
(58) Field of Search ............................. 435/232, 252.3, 435/320.1, 325, 69.1; 536/23.2; 530/350

(56) References Cited

PUBLICATIONS

Rokosz et al., Archives of Biochemistry and Biophysics 312:1–13, 1994.
Rokosz et al., Swiss Prot accession No. Q01581, 1994.

*Primary Examiner*—Rebecca E. Prouty
*Assistant Examiner*—Delia M. Ramirez
(74) *Attorney, Agent, or Firm*—Celera Genomics; Justin D. Karjala

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

12 Claims, 26 Drawing Sheets

```
   1 CGCTCCCAG CGACTCTCGG CAGTGCCGGA GTCGGGTGGG TTGGCGGCTA
  51 TAAAGCTGGT AGCGAAGGGG AGGCGCGCGG GACTGTCCCT TCGTGGCTCA
 101 CTCCCTTTCC TCTGCTGCCG CTCGGTCACG CTTGCTCTTT CACCATGCCT
 151 GGATCACTTC CTTTGAATGC AGAAGCTTGC TGGCCAAAAG ATGTGGGAAT
 201 TGTTGCCCTT GAGATCTATT TTCCTTCTCA ATATGTTGAT CAAGCAGAGT
 251 TGAAAAATA TGATGGTGTA GATGCTGGAA AGTATACCAT TGGCTTGGGC
 301 CAGGCCAAGA TGGGCTTCTG CACAGATAGA GAAGATATTA ACTCTCTTTG
 351 CATGACTGTG GTTCAGAATC TTATGGAGAG AAATAACCTT TCCTATGATT
 401 GCATTGGGCG GCTGGAAGTT GGAACAGAGA CAATCATCGA CAAATCAAAG
 451 TCTGTGAAGA CTAATTTGAT GCAGCTGTTT GAAGAGTCTG GGAATACAGA
 501 TATAGAAGGA ATCGACACAA CTAATGCATG CTATGGAGGC ACAGCTGCTG
 551 TCTTCAATGC TGTTAACTGG ATTGAGTCCA GCTCTTGGGA TGGGCTTGT
 601 GGGACACATA TGCAACATGC CTATGATTTT TACAAGCCTG ATATGCTATC
 651 TGAATATCCT ATAGTAGATG GAAAACTCTC CATACAGTGC TACCTCAGTG
 701 CATTAGACCG CTGCTACTCT GTCTACTGCA AAAAGATCCA TGCCCAGTGG
 751 CAGAAAGAGG GAAATGATAA AGATTTTACC TTGAATGATT TTGGCTTCAT
 801 GATCTTTCAC TCACCATATT GTAAACTGGT TCAGAAATCT CTAGCTCGGA
 851 TGTTGCTGAA TGACTTCCTT AATGACCAGA ATAGAGATAA AAATAGTATC
 901 TATAGTCCCC TCCAACCCTT TGCCGATGTT AAATTAGAAG ACACCTACTT
 951 TGATAGAGAT GTGGAGAAGG CATTTATGAA GGCTAGCTCT GAACTCTTCA
1001 GTCAGAAAAC AAAGGCATCT TTACTTGTAT CAAATCAAAA TGGAAATATG
1051 TACACATCTT CAGTATATGG TTCCCTTGCA TCTGTTCTAG CACAGTACTC
1101 ACCTCAGCAA TTAGCAGGGA AGAGAATTGG AGTGTTTCT TATGGTTCTG
1151 GTTTGGCTGC CACTCTGTAC TCTCTTAAAG TCACACAAGA TGCTACACCG
1201 GGGTCTGCTC TTGATAAAAT AACAGCAAGT TTATGTGATC TTAAATCAAG
1251 GCTTGATTCA AGAACTGGTG TGGCACCAGA TGTCTTCGCT GAAAACATGA
1301 AGCTCAGAGA GGACACCCAT CATTGGTCA ACTATATTCC CCAGGTTCA
1351 ATAGATTCAC TCTTTGAAGG AACGTGGTAC TTAGTTAGGG TGGATGAAAA
1401 GCACAGAAGA ACTTACGCTC GGCGTCCAC TCCAAATGAT GACACTTTGG
1451 ATGAAGGAGT AGGACTTGTG CATTCAAACA TAGCAACTGA GCATATTCCA
1501 AGCCCTGCCA AGAAAGTACC AAGACTCCCT GCCACAGCAG CAGAACCTGA
1551 AGCAGCTGTC ATTAGTAATG GGAACATTA AGATACTCTG TGAGGTGCAA
1601 GACTTCAGGG TGGGGTGGGC ATGGGGTGGG GGTATGGGAA CAGTTGGAGG
1651 AATGGGATAT CTGGGGATAA TTTTAAAGGA TTACATGTTA TGTAAATTTT
1701 TATGTGACTG ACATGGAGCC TGGATGACTA TCGTGTACTT GGGAAAGTCT
1751 CTTTGCTCTA TTTGCTGACA TGCTTCCTGT TGTGGTCTGG CCAATGCCAA
1801 ATGTACTCGA ATGATGTTAA GGGCTCTGTA AAACTTCATA CCTCTTTGGC
1851 CATTTGTATG CATGATGTTT GGTTTTTAAA CATGGTATAA TGAATTGTGT
1901 ACTTCTGTCA GAAGAAAGCA GAGGTACTAA TCTCCAATTA AAAAATTTT
1951 TAACATGTAA AAAAAAAAA AAAAAAAAA AAAAAAAAA AAAAAAAAA
2001 AA    (SEQ ID NO:1)
```

FIGURE 1A

FEATURES:
5'UTR:       1-144
Start Codon: 145
Stop Codon:  1579
3'UTR:       1582

Homologous proteins:
Top 10 BLAST Hits

|  | Score | E |
|---|---|---|
| CRA|18000004923628 /altid=gi|4504429 /def=ref|NP_002121.1| 3-hy... | 961 | 0.0 |
| CRA|18000004928954 /altid=gi|284048 /def=pir||S27197 hydroxymet... | 945 | 0.0 |
| CRA|18000004939530 /altid=gi|8393538 /def=ref|NP_058964.1| 3-hy... | 915 | 0.0 |
| CRA|18000004933126 /altid=gi|123332 /def=sp|P13704|HMCS_CRIGR H... | 912 | 0.0 |
| CRA|18000004944250 /altid=gi|123331 /def=sp|P23228|HMCS_CHICK H... | 811 | 0.0 |
| CRA|18000004996464 /altid=gi|86312 /def=pir||S13887 hydroxymeth... | 810 | 0.0 |
| CRA|108000024648192 /altid=gi|12731376 /def=ref|XP_011295.1| 3-... | 673 | 0.0 |
| CRA|18000004879762 /altid=gi|1708233 /def=sp|P54870|HMC2_BLAGE ... | 489 | e-137 |
| CRA|18000005054533 /altid=gi|7436678 /def=pir||T09688 hydroxyme... | 384 | e-105 |
| CRA|271273992 /altid=gi|7799986 /def=gb|AAF69804.1|AF148847_1 (... | 377 | e-103 |

BLAST dbEST hits:

|  | Score | E |
|---|---|---|
| gi|10952250 /dataset=dbest /taxon=96... | 1247 | 0.0 |
| gi|6854981 /dataset=dbest /taxon=9606... | 1068 | 0.0 |
| gi|10992587 /dataset=dbest /taxon=96... | 894 | 0.0 |
| gi|12762375 /dataset=dbest /taxon=960... | 890 | 0.0 |
| gi|11125858 /dataset=dbest /taxon=96... | 890 | 0.0 |
| gi|7376370 /dataset=dbest /taxon=9606... | 890 | 0.0 |
| gi|10991736 /dataset=dbest /taxon=96... | 884 | 0.0 |
| gi|10992783 /dataset=dbest /taxon=96... | 882 | 0.0 |
| gi|10990968 /dataset=dbest /taxon=96... | 882 | 0.0 |

EXPRESSION INFORMATION FOR MODULATORY USE:
library source:
From BLAST dbEST hits:
gi|10952250 Teratocarcinoma
gi|6854981 Fetal brain
gi|10992587 Teratocarcinoma
gi|12762375 Liver- adenocarcinoma
gi|11125858 Lung small cell carcinoma
gi|7376370 Genitourinary tract

FIGURE 1B gi|10991736 Teratocarcinoma
gi|10992783 Teratocarcinoma
gi|10990968 Teratocarcinoma neuronal repcursor cells From tissue screening panels:
Whole liver

FIGURE 1C

```
  1 MPGSLPLNAE ACWPKCVGIV ALEIYFPSQY VDQAELEKYD GVDAGKYTIG
 51 LGQAKMGFCT DREDINSLCM TVVQNLMERN NLSYDCIGRL EVGIETIIDK
101 SKSVKINLMQ LFEESGNTDI EGIDTINACY GGTAAVENAV NWIESSSWDG
151 LRGTHMQHAY DFYKPDMLSE YPIVDGKLSI QCYLSALDRC YSVYCKKIHA
201 QWQKEGNDKD FTINDFGFMI FHSPYCKLVQ KSLARMLLND FLNDQNRDKN
251 STYSGLFAFG DVKLEDTYFD RDVEKAFMKA SSELFSQKTK ASLLVSNQNG
301 NMYTSSVYGS LASVLAQYSP QQLAGKRIGV FSYGSGLAAT LYSLKVTQDA
351 TPGSALDKIT ASLCDLKSRL DSRTGVAPDV FAENMKLRED THHLVNYIPQ
401 GSIDSLFEGT WYLVRVDEKH RRTYARRPTP NDDTLDEGVG LVHSNIATEH
451 IPSPAKKVPR LPATAAEPEA AVISNGEH  (SEQ ID NO:2)
```

FEATURES:
Functional domains and key regions:
[1] PDOC00001 PS00001 ASN_GLYCOSYLATION
N-glycosylation site 81-84 NLSY

[2] PDOC00004 PS00004 CAMP_PHOSPHO_SITE
cAMP- and cGMP-dependent protein kinase phosphorylation site 426-429 RRPT

[3] PDOC00005 PS00005 PKC_PHOSPHO_SITE
Protein kinase C phosphorylation site

Number of matches: 4
    1    60-62  TDR
    2    103-105  SVK
    3    286-288  SQK
    4    343-345  SLK

[4] PDOC00006 PS00006 CK2_PHOSPHO_SITE
Casein kinase II phosphorylation site

Number of matches: 16
    1    60-63  TDRE
    2    96-99  TIID
    3    118-121  TDIE
    4    146-149  SSWD
    5    185-188  SALD
    6    354-357  SALD
    7    212-215  TLND
    8    254-257  SGLE
    9    267-270  TYFD
    10    185-188  SALD

FIGURE 2A

| | | |
|---|---|---|
| 11 | 354-357 | SALD |
| 12 | 362-365 | SLCD |
| 13 | 368-371 | SRLD |
| 14 | 405-408 | SLFE |
| 15 | 429-432 | TPND |
| 16 | 434-437 | TLDE |

[5] PDOC00008 PS00008 MYRISTYL
N-myristoylation site

Number of matches: 11

| | | |
|---|---|---|
| 1 | 41-46 | GVDAGK |
| 2 | 50-55 | GLGQAK |
| 3 | 122-127 | GIDTTN |
| 4 | 131-136 | GGTAAV |
| 5 | 150-155 | GLRGTH |
| 6 | 300-305 | GNMYTS |
| 7 | 309-314 | GSLASV |
| 8 | 334-339 | GSGLAA |
| 9 | 336-341 | GLAATL |
| 10 | 401-406 | GSIDSL |
| 11 | 440-445 | GLVHSN |

[6] PDOC00009 PS00009 AMIDATION
Amidation site 324-327 AGKR

[7] PDOC00942 PS01226 HMG_COA_SYNTHASE
Hydroxymethylglutaryl-coenzyme A synthase active site 117-132 NIDIEGIDTTNACYGG Membrane spanning structure and domains:

| Helix | Begin | End | Score | Certainty |
|---|---|---|---|---|
| 1 | 300 | 320 | 0.990 | Putative |
| 2 | 327 | 347 | 1.033 | Certain |

FIGURE 2B

BLAST Alignment to Top Hit:
>CRA|18000004923628 /altid=gi|4504429 /def=ref|NP_002121.1|
        3-hydroxy-3-methylglutaryl-Coenzyme A synthase 1
        (soluble); 3-hydroxy-3-methylglutaryl-Coenzyme A synthase
        1 [Homo sapiens] /org=Homo sapiens /taxon=9606
        /dataset=nraa /length=520
    Length = 520

Score =  961 bits (2458), Expect = 0.0
 Identities = 478/520 (91%), Positives = 478/520 (91%), Gaps = 42/520 (8%)
 Frame = +1

Query: 145   MPGSLPLNAEACWPKDVGIVALEIYFPSQYVDQAELEKYDGVDAGKYTIGLGQAKMGFCT 324
             MPGSLPLNAEACWPKDVGIVALEIYFPSQYVDQAELEKYDGVDAGKYTIGLGQAKMGFCT
Sbjct: 1     MPGSLPLNAEACWPKDVGIVALEIYFPSQYVDQAELEKYDGVDAGKYTIGLGQAKMGFCT 60

Query: 325   DREDINSLCMTVVQNLMERNNLSYDCIGRLEVGTETIIDKSKSVKINLMQLFEESGNTDI 504
             DREDINSLCMTVVQNLMERNNLSYDCIGRLEVGTETIIDKSKSVKINLMQLFEESGNTDI
Sbjct: 61    DREDINSLCMTVVQNLMERNNLSYDCIGRLEVGTETIIDKSKSVKINLMQLFEESGNTDI 120

Query: 505   EGIDTINACYGGTAAVFNAVNWIESSSWDG------------------------------ 594
             EGIDTINACYGGTAAVFNAVNWIESSSWDG
Sbjct: 121   EGIDTINACYGGTAAVFNAVNWIESSSWDGRYALVVAGDIAVYATGNARPTGGVGAVALL 180

Query: 595   ------------LRGIHMQHAYDFYKPDMLSEYPIVDGKLSIQCYLSALDRCYSVYCKKI 738
                         LRGIHMQHAYDFYKPDMLSEYPIVDGKLSIQCYLSALDRCYSVYCKKI
Sbjct: 181   IGPNAPLIFERGLRGIHMQHAYDFYKPDMLSEYPIVDGKLSIQCYLSALDRCYSVYCKKI 240

Query: 739   HAQWQKEGNDKDFTLNDFGFMIFHSPYCKLVQKSIARMLINDFTNDQNRDKNSIYSGLEA 918
             HAQWQKEGNDKDFTLNDFGFMIFHSPYCKLVQKSLARMLLNDFLNDQNRDKNSIYSGLEA
Sbjct: 241   HAQWQKEGNDKDFTLNDFGFMIFHSPYCKLVQKSLARMLLNDFLNDQNRDKNSIYSGLEA 300

Query: 919   FGDVKLEDTYFDRDVEKAFMKASSELFSQKTKASLLVSNQNGNMYTSSVYGSLASVLAQY 1098
             FGDVKLEDTYFDRDVEKAFMKASSELFSQKTKASLLVSNQNGNMYTSSVYGSLASVLAQY
Sbjct: 301   FGDVKLEDTYFDRDVEKAFMKASSELFSQKTKASLLVSNQNGNMYTSSVYGSLASVLAQY 360

Query: 1099  SPQQLAGKRIGVFSYGSGLAATLYSLKVTQDATPGSALDKITASLCDLKSRLDSRTGVAP 1278
             SPQQLAGKRIGVFSYGSGLAATLYSLKVTQDATPGSALDKITASLCDLKSRLDSRTGVAP
Sbjct: 361   SPQQLAGKRIGVFSYGSGLAATLYSLKVTQDATPGSALDKITASLCDLKSRLDSRTGVAP 420

Query: 1279  DVFAENMKLREDTHHLVNYIPQGSIDSLFEGIWYLVRVDEKHRRTYARRPTPNDDTLDEG 1458
             DVFAENMKLREDTHHLVNYIPQGSIDSLFEGIWYLVRVDEKHRRTYARRPTPNDDTLDEG
Sbjct: 421   DVFAENMKLREDTHHLVNYIPQGSIDSLFEGIWYLVRVDEKHRRTYARRPTPNDDTLDEG 480

FIGURE 2C

```
Query: 1459  VGLVHSNIATEHIPSPAKKVPRLPATAAEPEAAVISNGEH 1578
             VGLVHSNIATEHIPSPAKKVPRLPATAAEPEAAVISNGEH
Sbjct: 481   VGLVHSNIATEHIPSPAKKVPRLPATAAEPEAAVISNGEH 520   (SEQ ID NO:4)

>CRA|18000004928954 /altid=gi|284048 /def=pir||S27197
            hydroxymethylglutaryl-CoA synthase (EC 4.1.3.5),
            cytosolic, fibroblast isoform - human /org=human
            /taxon=9606 /dataset=nraa /length=520
         Length = 520

Score = 945 bits (2417), Expect = 0.0
 Identities = 471/518 (90%), Positives = 472/518 (90%), Gaps = 42/518 (8%)
 Frame = +1

Query: 145   MPGSLPLNAEACWPKDVGIVALEIYFPSQYVDQAELEKYDGVDAGKYTIGLGQAKMGFCT 324
             MPGSLPLNAEACWPKDVGIVALEIYFPSQYVDQAELEKYDGVDAGKYTIGLGQAKMGFCT
Sbjct: 1     MPGSLPLNAEACWPKDVGIVALEIYFPSQYVDQAELEKYDGVDAGKYTIGLGQAKMGFCT 60

Query: 325   DREDINSLCMTVVQNLMERNNLSYDCIGRLEVGTETIIDKSKSVKTNLMQLFEESGNTDI 504
             DREDINSLCMTVVQNLMERNNLSYDCIGRLEVGTETIIDKSKSVKTNLMQLFEESGNTDI
Sbjct: 61    DREDINSLCMTVVQNLMERNNLSYDCIGRLEVGTETIIDKSKSVKTNLMQLFEESGNTDI 120

Query: 505   EGIDTTNACYGGTAAVFNAVNWIESSSWDG--------------------------- 594
             EGIDTTNACYGGTAAVFNAVNWIESSSWDG
Sbjct: 121   EGIDTTNACYGGTAAVFNAVNWIESSSWDGRYALVVAGDIAVYATGNARPTGGVGAVALL 180

Query: 595   ------------LRGTHMQHAYDFYKPDMLSEYPIVDGKLSIQCYLSALDRCYSVYCKKI 738
                         LRGTHMQHAYDFYKPDMLSEYPIVDGKLSIQCYLSALDRCYSVYCKKI
Sbjct: 181   IGPNAPLIFERGLRGTHMQHAYDFYKPDMLSEYPIVDGKLSIQCYLSALDRCYSVYCKKI 240

Query: 739   HAQWQKEGNDKDFTLNDFGFMIFHSPYCKLVQKSLARMLLNDFINQNRDKNSIYSGLEA 918
             HAQWQKE ND DFT NDFGFMIFHSPYCKLVQKSLARMLLNDFINQNRDKNSIYSGL+A
Sbjct: 241   HAQWQKEANDNDFTINDFGFMIFHSPYCKLVQKSLARMLLNDFINQNRDKNSIYSGLKA 300

Query: 919   FGDVKLEDTYFDRDVEKAFMKASSELFSQKTKASLLVSNQNGNMYTSSVYGSLASVLAQY 1098
             FGDVKLEDTYFDRDVEKAFMKASSELFSQKTKASLLVSNQNGNMYTSSVYGSLASVLAQY
Sbjct: 301   FGDVKLEDTYFDRDVEKAFMKASSELFSQKTKASLLVSNQNGNMYTSSVYGSLASVLAQY 360

Query: 1099  SPQQLAGKRIGVFSYGSGLAATLYSLKVIQDATPGSALDKITASLCDLKSRLDSRTGVAP 1278
             SPQ LAGKRIGVFSYGSGLAATLYSLKVIQDATPGSALDKITASLCDLKSRLDSRTGVA
Sbjct: 361   SPQHLAGKRIGVFSYGSGLAATLYSLKVIQDATPGSALDKITASLCDLKSRLDSRTGVAQ 420
```

FIGURE 2D

```
Query: 1279 DVFAENMKLREDTHHLVNYIPQGSIDSLFEGIWYLVRVDEKHRRTYARRPTPNDDTLDEG 1458
             DVFAENMKLREDTHHLVNYIPQGSIDSLFEGIWYLVRVDEKHRRTYARRPTPNDDTLDEG
Sbjct:  421  DVFAENMKLREDTHHLVNYIPQGSIDSLFEGIWYLVRVDEKHRRTYARRPTPNDDTLDEG  480

Query: 1459 VGLVHSNIATEHIPSPAKKVPRLPATAAEPEAAVISNG 1572
             VGLVHSNIATEHIPSPAKKVPRLPATAAEPEAAVISNG
Sbjct:  481  VGLVHSNIATEHIPSPAKKVPRLPATAAEPEAAVISNG  518   (SEQ ID NO:5)

Hmmer search results (Pfam):
Model    Description                                    Score    E-value  N
PF01154  Hydroxymethylglutaryl-coenzyme A synthase      1050.3     0      2

Parsed for domains:
Model    Domain  seq-f  seq-t    hmm-f  hmm-t    score    E-value
PF01154   1/2      13    150 ..    1     138 [.   409.2   3.8e-119
PF01154   2/2     151    427 ..   181     461 .]   635.2   3.6e-187
```

FIGURE 2E

```
   1 CCATTTTTCC CGCCATCACT GTCTTTAAAT TAGTCCATCG GAATTAGTTT
  51 AGCCTGTGCA GTCTAACCCT AGCCAATAAG GGAACGACAC AGCAGTGGGG
 101 ACCACGTGCG TCAGGAATAA GAACCCCTTT CCCTCCCTCG TCCAAGTGTG
 151 CACTCACCAT TGCTCCATCT GTAAGGGTGC ACCCTTCTAT AGAAGTACCT
 201 TGCCTTGCTG AGAATTAAAA AGAAAATTTT ATATTGGACT GCTATTTCTT
 251 TTGCAGCATG GAAACTTTAT TTATAACAAG ATCTTCTGTA TCTAATTACT
 301 AACCCTTTTT GTTCTCCATT GCTTGGCTTC CCAGTAATCA ATAATCATGC
 351 TCACTTTGCT TAATTGAAGA TTAACGTGAT CAAAAAGACG GTCTGTTCCT
 401 TGTAGAAATT TCCGGTTGTG TAAGATGGTC ATTCTCATGA CCGTCTGGCT
 451 AATCATTTCC CATTATGTAC TCCTGGAGTT GGAATTATTT GCGATTCCTA
 501 ACGACAAAAC TGTATCTCT TTCTTGTGTT TGTCCTTACT GCCTTTCAGC
 551 ATATTCCAAT ATGCCAAGAA TTTTAATCTC CTACCCCACC CCAAATTGCT
 601 GTTGATCATA ATCAGGCAAT GTCTCTCTCT CTGTTTACTA TCTAGTTACT
 651 TTACATACAT ATGAAGTGAG TCATGGGCAA TACTGTGGAA TGGAAATCAT
 701 TACTGAGTGG TCCTCTTCCC CCAAGTCATT TATGCCACCA CTTCACAGTG
 751 GTTCCATTTC CAATATATTT TGCCACTTTG CTGCTGAGAA TGTGTCTTAC
 801 TAGGTTAGCA TCTATAGTGG TTAAAAGAAT CTCCCATAAC AATAATGTG
 851 TGAATCACAG AATTACCAAT GACCCCTTAT CAATAGCATT CCTGTTAATT
 901 AAATTGAGAT GGGAGAGAC ACAAACAACT CCGAACCTCA CTCATGGTCC
 951 CCCACCAAAG CTAAGTATTA TGGCTTCTCT CTCTGACCAG ATAGAGGCAG
1001 AGTTTATTGC AAAGCCACAA GTGTCCTCCT TTGGATTCCC CCAAATAGTG
1051 TTTCAGTGAA TTCCTCTAGC TTGAATTGCT CCTCTCTATT TGCTGGGGA
1101 GTTAGGCAGT CCGTATCCGA TGGATTTACT ATGCCGACAA TTACGTGGCC
1151 TTTCCACAGC CTTTTACTTG GCAGGTACCA CATATGAAGC TTAGAAGATA
1201 CAGTGGGCAA CAGGCCAAAT GGAGTCCCTT TCCTCAGAGT GCATGGCCTG
1251 GCAAAAATCC TTGAATTCAG TATCAACTTC CCTTCACAGG CAAGGCTCTG
1301 CACCCTCCCC ACGGATGCCT AATCCTGAAA CCATTTTGTT TTAGGTTTAG
1351 TTACAAAGCT TTGTCTCAAG AGCACTTTTG TTTGTTCTGT TTTCTTTAAG
1401 TCAACGTAGT TTTGAATAAA GGAGACAATN ATTTGAGTAT TTACAAATCG
1451 GGTATTTAGA CTATTTACAC ATATACAAGT TCTGGGTGAA GTATTCTGCT
1501 CCAATTTGCA ATCTACGCAC ACTTTGCTAG AAAACGTTAA GACTGAATTC
1551 AAATCAAGTA CAGTATTTCA GAAATCTTTC AGGTGAAGCC TAGTTCTGGT
1601 TGCTAGGCAA CCTGACAGAC TCCCAAGCTG GGACCACCTC GCCTCCCACA
1651 TTTGACCATC TCTCCAGCCG TGGGACGCGG AGTACCCATT GGCCCGCATC
1701 TCCTCTCACT TAGTCCCAAT TGGTCGGAGA ACCTCTCACT CCGCTCCCGT
1751 TGGCTCTCGC CGTATCTGC AGCTCCGTCA TTGGCAACTG GCTCTCGTG
1801 CCACCTCACG TCAGTCTCTC ACACCACTTC CTGGCCCTG AGACTTTGTC
1851 CCCGCCTCTT CTCCCCGCCC TTCCAGCCAC GAGGGAAAAT CCTAGCGAGT
1901 CATCGCCTCT AGTTTCCTTT TGATTGGTAG AAGCCGGACT GGGGGCGGG
1951 CGCTGCCGGG CAACTCTACC GGCCGCGATT GGCTGTGGGA GCCACCGTCC
2001 CGCCTCCTAG CGACTCTCGG CGGTGCCGGA GTCGGGTGGG TTGCGGGCTA
2051 TAAAGCTGGT GGCGAAGGGG AGGCGCCGCG GACTGTCCTT TGGTGGCTCA
2101 CTCCCTTTCC TCTGCTGCCG CTCGGTCACG CTTGGTGAGT GTCCCGCGCT
2151 GGGGAGTAGA ACTGGGCTGC GGAGGTGCCG CGGCGGGGT GTGGCCAGA
2201 CAGAGGCGGT GTCCTTGACT AGGCCCGAAG GAGCTGGGGC TCTGGTCAG
2251 GACGTAGGCG TGGACTTTGC CCGGGAGGAT GGGCACCGT GAGCGGGCC
```

FIGURE 3A

```
2301 GGGCGGGGGT TCCCTCGTGA GGCACCTGAG GCCGACCGTA GCGGATCTGA
2351 GAAGATCCGA GAACACAGGC GAGTCCCCGA GCCGAGAACG CGAGACGGCG
2401 TTGAGGTCTA GGTATTCTAA CGACAGAGGA GTTGGAGGTC CCAGAGACGC
2451 AGCTGTGACC GCCTAGAGGT GAGTGGGCGG TGTCAGGACC CCGAGAGAAG
2501 ACAGTTGGGC TACCAAGGCG TTTCCAGAGC GTTGGTAAAG GGTGGACGCC
2551 AAAGGATGGG CAAGATCCTC TTTAGACGGA GGCTGGTAGG TTCGCAGGGG
2601 GTGTGTCCTG CTGCCACATA TAGAGTTGAT GGAAAGAAGG GAAGTGGGTA
2651 GCATTACTTT TCTTCCTCAG CTCAGGTGCA AGAAAGCGTT CACAACCGTG
2701 ATTTAGACCT GGCTAAGTAC TGGGGCTCAG TCTGTACTTG CTTCAAATCT
2751 CATAGATCAC TGCCTCCGGC CTTCCTGCCT CCATATTTTT TTTGTCTAC
2801 GTTTTAAAAA ATAGGCTTCC TTGGTGTTCT GAAATCCCAC ATCTCTCTCC
2851 TACTAATACC TTCGGGACCA GCTTTAGGTG ATACAGTGTA ATGGGCAGGC
2901 ACTCACAGAG TCCTCCCACA AATAGGTTTT GGATTAAGCT AAGGATATTT
2951 CAAAGCAAGT ATATGGAGTC TTTGAAAACC CACGTCTGGC CTTGACCAGT
3001 GGTAGAGAAA CGATTATTCT GATCCACTCT GGAGGAGGGA TTTGGGGAAC
3051 AAATAATGTG AGGTTGTGCC TGTTTGTCAT GCTTGTCCCT ATGGCCTTAG
3101 CCTTAAGGCA TCAGTAGCTG CTTTCACTGC TCACCTCTGC TGCAGCTCCC
3151 CACCTTCCCG AGGATGCTCT TGCCACCTGC TGCAGTAGGA TGATGTGTTC
3201 TGGTTGCTGC TAACTAACAT TTGCTCTGTT TTAGGCATGA ATATGAAAAA
3251 CAATGACAAG ATAAACAACA AAATTAAGAC AAATGGAAGT GCTCCTAGAG
3301 TTAACAGATT TTTCCTTCTG AGATGTGTTT TGGACTTTAT TGCACAGATA
3351 CTATTAGATG AGAGGCAGTT GAAAGTCGTT AACATTACCC GTGTCAGTAG
3401 TTCTTTGCAC TTGAGACACC TAAGCAGCTT GTGTTCTTTA AACTTTATTT
3451 TAAAATTGCA GTTATTTTTG TGTGAAGAAG GGGGCAGGGA TAGCATACCT
3501 TATGGGAAGA GACAAAGGCT TTCTTTGTGT CTACCTTTGT AGATATTTCT
3551 CACCTAAGTT TGTAAGTTTG CCCTTTATTC GGTTCTACTT TAGTTCAGCT
3601 CAATTCTAGT ATAATCATCA GTAACCCCAG CACTCAGAAG GTCTGACTTA
3651 CGCTGTGGGG AGCCAGTGTA AAAGGATATT TTATGTTTGG AGCCATAGCC
3701 CACATCATTT GGGCCTTGTT TTAATTTTGT TTTTCATCTT AAATATCCCT
3751 CCAGATTGCT TTTACATCTT GTTTCTTTTA ACTGTGGATT GATTTTGAGA
3801 TTTTGACTTA GATTTTAGAT AGCTTTTCTC AGAAGAAATA AACGCTAAAA
3851 CCCGATATTG TTGTAACATC AGTTTCCTGT GTCCTCTAGA ATCATTTAAA
3901 ACCTGGTTGG ATCTTCCATA ATCCAGTGGA ATTGGATATG AGATGTAGCT
3951 GGAGAAGTTT GTTTTGCTAC ATATCAGAAT CTCCAATTAG TTTCATTTAG
4001 AAAGGAATAT AGCCTTATAA TTTTATGCTG GGTTACTGTG GAACCAAATA
4051 TCATAGAAGG ATGTGTGATA TTTTTATGTT TTTCAAGAAG GTAGTATAGA
4101 TTTAAAAGGT GGGATACATA TTACCTGTCC TAATGATAGG ACTAGATTTT
4151 TTTTTTTTTT TTTTTGGGG AGACAGAATC TGGCTCTGTC GCCCAAGCTG
4201 GAGTGCAGCA GCGTGATCTC GGCTCACTGC AACTTATGCC TCCCAGTGAT
4251 TCTCCTGCCT CAGCCTCCCA AGTAGCTGGG ACTACCGGCA TGTGCCACCA
4301 CACCCAGCTA ATTTTTTTGT ATTTTTAGAA GAGATGGGGT GTCACCATGT
4351 TGGTCAGACT GGTCTTGAAC TCCTGACCTC AAATGATCCG TCCCCCTTGG
4401 CCTCCCAAAG TGCTGAGATT ACAGGCGTGA GCCACCATGC CTGGCTAGAA
4451 CTAGACTCTT AATCTCTTCA TCCTAATGCA TGGCGTGTGT TGATGTTCAC
4501 TTAATGTCTG TCAACTGGGT GTAGTTACAC CAGTAGCGGA GAGGCTAATC
4551 TTTGAAAGCC TGAAGTGTTG TCTTCATCTT TGCAGGGTTT TTAGTTGTGG
```

FIGURE 3B

```
4601 GTGCATATGG GAATGATTGT AAGACCAACA AATGTTTTCT GATTCCATAT
4651 GGGCTTCTTA CATTTTTCAC CTTGGAATCT GGGAACAATT GAAACCTACC
4701 ATATGCCTTG AACAGTAGCA GTAAAGAGCC AGTTTCTTTA AACTAGACAT
4751 TATGGTGCTG CAGCTCATCT CAAAACTGAT AGCAGGCTAC TCTGGACACA
4801 CTACATATAG AGTAGCCCTG CTCTGCAAGG AGCAGTAATA AATTAAAAAA
4851 AAAATTAAAA AGTGATAGCA GAAAGCACTT ACTACTGACG GCTGCTACAA
4901 GTATTAAATC TAAAAGATTT GTCCTCTAGT AGTTATAACT CCAAATTCAG
4951 CCACTGAAAA ATGTGACATT TGAGTACCCT TTACTTCAAG GTCTCAAAGG
5001 GATTTCAAAA AATCAAAATA TATAGCCCCT CTCCCAAAAG AAGTGTAGGA
5051 ATCCTGTATG GATAAGAAGA CTGCCCATAA CTAGTTTTCC ATAGAGAGTA
5101 GGCTATGTAG ACTTGGGTAT GAATGACCTA CCTCTGTAGA AGTGCAGGTC
5151 CCTGATTAGA AAACTTATTT TCTGTGTGAT TTATCGAGGA AAGCTTCCAG
5201 GAAGAGGTGA CTTAGAACAG GGCCTTGAAG ATGAGTAGAA TCTCTGATAC
5251 GCAGACCAGT AACCTGGGA GGAGGCAGGG ATGTCCATGC TTTTACTTG
5301 GAGAACTATA CCAGAGTGTA CAGGTTTCAG CAAGTCTTTC TTAACATTAG
5351 TTTTTACTTG CTTGCTCCTA AGGAGGAAAG GTTGCCAACT TGTTCTTAAT
5401 TTCCTAGATT TATCTCCTGT AACAATGAGA AAGATCAATA GGTAACTGTT
5451 TATATTTAT AGTTTACATA CCAAAATGTG TAGGCAATGA ACTTCTCCAA
5501 CCACTTCTTT GAATCAAGGC TAAGGAGGGA GCCAGAAGGA AGTATTCAGA
5551 ACACTGAGTA AACTCCAGAA GAAACTACCA TTGCATAAAT CTGGTTGGCC
5601 CTAGGCAGTC TTATCATTCT TGTGTTTTAG TCTTTGCCAG ACTCAAAGTG
5651 CCTATATTTC ATCCCATGAG TCTGCAAACC TGCTTTGTGG TAACCTGCT
5701 GGCTACTTGC CATTCATTAA CTGCTTCTTG ACCCATGTTG ATTCCCTCTG
5751 TCACTTACTC TGAAAAGACC TGTTAGAAAT AAGCTTGTGA TCTGCTTGAG
5801 ACTTTGGCAA TACTGGTTTA GCCAGAATAG AGAAATCCTT AAGTAGCACA
5851 GCAATCCTTT CTGAATCTTC TATTTGTTTC TTCTTTGTTC TCTGTGTCTC
5901 TCCCACCTAA CATCCCTCTC CAATTTAAGT AATCAAAATA GAAAGAGGGG
5951 CCCAGGCAAG GTGGCCCACG CCTATAATCC CAGCACTTTG GGAGGCCAAA
6001 GTGGGTGGAT TGGTTTAGCC CAGGAGTTGG AGAACAGCCT GGGAAAGATG
6051 GCAAAACCCC ATCTCTACAA AAAATACAAA AATCAGCTGT GTATTGTGGC
6101 ATGTGCCTGT AGTCCCAGCT ACTTGCGGGG TCTGAGACAG GAGGATCACT
6151 TGAGCCTGGG AGGTCGAGGT TACAGTGAGC AGTGACTGGA ATGCTACTGC
6201 ATTCCAGTCT GGGTGACAGA GGGAGACCCT GTCTCAAAAA AAAAAAAAAA
6251 TTTGAGGGAA TATAGGCAGT GCAAGGAAAG GCAGAATATA GGCAGTTCAA
6301 GGAAAATTTC CTTGATACAA GTAGTGTCAA ATGCATATAC ATACATGAAC
6351 ATCAAGAAGA AATATTATTA TTTAAGTAGT CTTAACATGG AGAAGGAATC
6401 TTGTTTTTCA AGAACTGGTC TCTGTGGTCT GCTTAATTTG CAGAAGACAA
6451 AGGCATAATT TGAGATAATA AAGAACAAAG ATAGGTTATT TTCTCAAAGT
6501 ATGTATAATT ACAGTTAATT AGAGACATTT TTGGAATATT GTAGTATTCT
6551 TTGCCTACAA AACTCAAGAT CTATTTCTTT TTATGGGGCA GGGGGCGTA
6601 GGTGGGTAGT AAACTTAGTT AATGAAGTAA AAGGCGCTAC GACTGAAGAG
6651 CTCTTAAATT ATGTAATTAT GTAAAAAAAG TAAAGCTTTA TTAAATATTA
6701 ATAACATCCG AATGTAGTTA CCAGTGAATC CATTAAGGGC AGATGCTAAA
6751 TTGCCAGTA ATTAAATAGA GAGCAGACGA AATGGTGTAT GCTGTGTTAA
6801 ACATAGAAGT TGCCATCTCA AGTAACAATC AGTCTTTCAA AACAGATGGA
6851 CTGAAGAATA TGTTCCAGTC ACCTTCGCAA ATTATTTCTA CTTAATTTAC
```

FIGURE 3C

6901 ATAATAATGT TTAATGCTCC TTTGTCTAAA TGCTTAATTT TTTAACATAA
6951 GCAGTAAGAG GGAAAATCAC TTTATAAAAG GTTGGGAGGG TGAAGGTGGC
7001 AGTGTTGAAA ATGATTAGGT CTTGCTAGAA AAAATACCTT TATTTTCTTT
7051 GAAAAACACT TATAAGAACT ATAAGAACTA AGGTAATAGT CAGTGTATTG
7101 GTGCTTTGTG TTACAAAGTG TCTTCACATA TTTTATCATC TCAGCAATCC
7151 TTCACAATGA TCTGGGGAGG GCAACTGTAT TAGCTTCATT TTATAGATGA
7201 GGAAACTGAG GTCCAGAATT GCTCCCAAAG CCACAATCTG TTACATCCAG
7251 TGCAGGCTCT TGACTGCATA TATCTCTTTA CTCTAGAAAT TGCTAACTC
7301 ATTACAACTT GTTTATATTC CTTTCCCCCA ATTCTTGAAA ACCTTGGTTT
7351 AAAGCCTCAA TTGGTGACAT GGGCTTCTTA TTTCCTTGAG GTTTTTTGT
7401 TTATTCCTTC CTGCAATAGT AGGCTTCTTA TATCCGTTTA TTACCAGGAC
7451 TGAACCTTTC ACTATAAGGG CTATGAAAAT AAGGGGGAAA ATGTTCTATA
7501 AGCTTTAAGT ATGATTTTTT CTAAGCAAAT GTCAAATTCT ATTCTGCATA
7551 ATGTAATTGG ATAAGGAATT GCTTATTTTA ACTCACTTTG AATTGGATTC
7601 ATTAGTATTT GAATTTGGGT AGGATTTATA ACTTTAAAAG CANNNNNNN
7651 NNNNNNNNNN NNNNNNNNNN NNNNNNNNNN NNNNNNNNNN NNNNNNNNNN
7701 NNNNNNNNNN NNNNNNNNNN NNNNNNNNNN NNNNNNNNNN NNNNNNNNNN
7751 NNNNNNNNNN NNNNNNNNNN NNNNNNNNNN NNNNNNNNNN NNNNNNNNNN
7801 NNNNNNNNNN NNNNNNNNNN NNNNNNNNNN NNNNNNNNNN NNNNNNNNNN
7851 NNNNNNNNNN NNNNNNNNNN NNNNNNNNNN NNNNNNNNNN NNNNNNNNNN
7901 NNNNNNNNNN NNNNNNNNNN NNNNNNNNNN NNNNNNNNNN NNNNNNNNNN
7951 NNNNNNNNNN NNNNNNNNNN NNNNNNNNNN NNNNNNNNNN NNNNNNNNNN
8001 NNNNNNNNNN NNNNNNNNNN NNNNNNNNNN NNNNNNNNNN NNNNNNNNNN
8051 NNNNNNNNNN NNNNNNNNNN NNNNNNNNNN NNNNNNNNNN NNNNNNNNNN
8101 NNNNNNNNNN NNNNNNNNNN NNNNNNNNNN NNNNNNNNNN NNNNNNNNNN
8151 NNNNNNNNNN NNNNNNNNNN NNNNNNNNNN NNNNNNNNNN NNNNNNNNNN
8201 NNNNNNNNNN NNNNNNNNNN NNNNNNNNNN NNNNNNNNNN NNNNNNNNNN
8251 NNNNNNNNNN NNNNNNNNNN NNNNNNNNNN NNNNNNNNNN NNNNNNNNNN
8301 NNNNNNNNNN NNNNNNNNNN NNNNNNNNNN NNNNNNNNNN NNNNNNNNNN
8351 NNNNNNNNNN NNNNNNNNNN NNNNNNNNNN NNNNNNNNNN NNNNNNNNNN
8401 NNNNNNNNNN NNNNNNNNNN NNNNNNNNNN NNNNNNNNNN NNNNNNNNNN
8451 NNNNNNNNNN NNNNNNNNNN NNNNNNNNNN NNNNNNNNNN NNNNNNNNNN
8501 NNNNNNNNNN NNNNNNNNNN NNNNNNNNNN NNNNNNNNNN NNNNNNNNNN
8551 NNNNNNNNNN NNNNNNNNNN NNNNNNNNNN NNNNNNNNNN NNNNNNNNNN
8601 NNNNNNNNNN NNNNNNNNNN NNNNNNNNNN NNNNNNNNNN NNNNNNNNNN
8651 NNNNNNNNNN NNNNNNNNNN NNNNNNNNNN NNNNNNNNNN NNNNNNNNNN
8701 NNNNNNNNNN NNNNNNNNNN NNNNNNNNNN NNNNNNNNNN NNNNNNNNNN
8751 NNNNNNNNNN NNNNNNNNNN NNNNNNNNNN NNNNNNNNNN NNNNNNNNNN
8801 NNNNNNNNNN NNNNNNNNNN NNNNNNNNNN NNNNNNNNNN NNNNNNNNNN
8851 NNNNNNNNNN NNNNNNNNNN NNNNNNNNNN NNNNNNNNNN NNNNNNNNNN
8901 NNNNNNNNNN NNNNNNNNNN NNNNNNNNNN NNNNNNNNNN NNNNNNNNNN
8951 NNNNNNNNNN NNNNNNNNNN NNNNNNNNNN NNNNNNNNNN NNNNNNNNNN
9001 NNNNNNNNNN NNNNNNNNNN NNNNNNNNNN NNNNNNNNNN NNNNNNNNNN
9051 NNNNNNNNNN NNNNNNNNNN NNNNNNNNNN NNNNNNNNNN NNNNNNNNNN
9101 NNNNNNNNNN NNNNNNNNNN NNNNNNNNNN NNNNNNNNNN NNNNNNNNNN
9151 NNNNNNNNNN NNNNNNNNNN NNNNNNNNNN NNNNNNNNNN NNNNNNNNNN

FIGURE 3D

```
9201 NNNNNNNNNN NNNNNNNNNN NNNNNNNNNN NNNNNNNNNN NNNNNNNNNN
9251 NNNNNNNNNN NNNNNNNNNN NNNNNNNNNN NNNNNNNNNN NNNNNNNNNN
9301 NNNNNNNNNN NNNNNNNNNN NNNNNNNNNN NNNNNNNNNN NNNNNNNNNN
9351 NNNNNNNNNN NNNNNNNNNN NNNNNNNNNN NNNNNNNNNN NNNNNNNNNN
9401 NNNNNNNNNN NNNNNNNNNN NNNNNNNNNN NNNNNNNNNN NNNNNNNNNN
9451 NNNNNNNNNN NNNNNNNNNN NNNNNNNNNN NNNNNNNNNN NNNNNNNNNN
9501 NNNNNNNNNN NNNNNNNNNN NNNNNNNNNN NNNNNNNNNN NNNNNNNNNN
9551 NNNNNNNNNN NNNNNNNNNN NNNNNNNNNN NNNNNNNNNN NNNNNNNNNN
9601 NNNNNNNNNN NNNNNNNNNN NNNNNNNNNN NNNNNNNNNN NNNNNNNNNN
9651 NNNNNNNNNN NNNNNNNNNN NNNNNNNNNN NNNNNNNNNN NNNNNNNNNN
9701 NNNNNNNNNN NNNNNNNNNN NNNNNNNNNN NNNNNNNNNN NNNNNNNNNN
9751 NNNNNNNNNN NNNNNNNNNN NNNNNNNNNN NNNNNNNNNN NNNNNNNNNN
9801 NNNNNNNNNN NNNNNNNNNN NNNNNNNNNN NNNNNNNNNN NNNNNNNNNN
9851 NNNNNNNNNN NNNNNNNNNN NNNNNNNNNN NNNNNNNNNN NNNNNNNNNN
9901 NNNNNNNNNN NNNNNNNNNN NNNNNNNNNN NNNNNNNNNN NNNNNNNNNN
9951 NNNNNNNNNN NNNNNNNNNN NNNNNNNNNN NNNNNNNNNN NNNNNNNNNN
10001 NNNNNNNNNN NNNNNNNNNN NNNNNNNNNN NNNNNNNNNN NNNNNNNNNN
10051 NNNNNNNNNN NNNNNNNNNN NNNNNNNNNN NNNNNNNNNN NNNNNNNNNN
10101 NNNNNNNNNN NNNNNNNNNN NNNNNNNNNN NNNNNNNNNN NNNNNNNNNN
10151 NNNNNNNNNN NNNNNNNNNN NNNNNNNNNN NNNNNNNNNN NNNNNNNNNN
10201 NNNNNNNNNN NNNNNNNNNN NNNNNNNNNN NNNNNNNNNN NNNNNNNNNN
10251 NNNNNNNNNN NNNNNNNNNN NNNNNNNNNN NNNNNNNNNN NNNNNNNNNN
10301 NNNNNNNNNN NNNNNNNNNN NNNNNNNNNN NNNNNNNNNN NNNNNNNNNN
10351 NNNNNNNNNN NNNNNNNNNN NNNNNNNNNN NNNNNNNNNN NNNNNNNNNN
10401 NNNNNNNNNN NNNNNNNNNN NNNNNNNNNN NNNNNNNNNN NNNNNNNNNN
10451 NNNNNNNNNN NNNNNNNNNN NNNNNNNNNN NNNNNNNNNN NNNNNNNNNN
10501 NNNNNNNNNN NNNNNNNNNN NNNNNNNNNN NNNNNNNNNN NNNNNNNNNN
10551 NNNNNNNNNN NNNNNNNNNN NNNNNNNNNN NNNNNNNNNN NNNNNNNNNN
10601 NNNNNNNNNN NNNNNNNNNN NNNNNNNNNN NNNNNNNNNN NNNNNNNNNN
10651 NNNNNNNNNN NNNNNNNNNN NNNNNNNNNN NNNNNNNNNN NNNNNNNNNN
10701 NNNNNNNNNN NNNNNNNNNN NNNNNNNNNN NNNNNNNNNN NNNNNNNNNN
10751 NNNNNNNNNN NNNNNNNNNN NNNNNNNNNN NNNNNNNNNN NNNNNNNNNN
10801 NNNNNNNNNN NNNNNNNNNN NNNNNNNNNN NNNNNNNNNN NNNNNNNNNN
10851 NNNNNNNNNN NNNNNNNNNN NNNNNNNNNN NNNNNNNNNN NNNNNNNNNN
10901 NNNNNNNNNN NNNNNNNNNN NNNNNNNNNN NNNNNNNNNN NNNNNNNNNN
10951 NNNNNNNNNN NNNNNNNNNN NNNNNNNNNN NNNNNNNNNN NNNNNNNNNN
11001 NNNNNNNNNN NNNNNNNNNN NNNNNNNNNN NNNNNNNNNN NNNNNNNNNN
11051 NNNNNNNNNN NNNNNNNNNN NNNNNNNNNN NNNNNNNNNN NNNNNNNNNN
11101 NNNNNNNNNN NNNNNNNNNN NNNNNNNNNN NNNNNNNNNN NNNNNNNNNN
11151 NNNNNNNNNN NNNNNNNNNN NNNNNNNNNN NNNNNNNNNN NNNNNNNNNN
11201 NNNNNNNNNN NNNNNNNNNN NNNNNNNNNN NNNNNNNNNN NNNNNNNNNN
11251 NNNNNNNNNN NNNNNNNNNN NNNNNNNNNN NNNNNNNNNN NNNNNNNNNN
11301 NNNNNNNNNN NNNNNNNNNN NNNNNNNNNN NNNNNNNNNN NNNNNNNNNN
11351 NNNNNNNNNN NNNNNNNNNN NNNNNNNNNN NNNNNNNNNN NNNNNNNNNN
11401 NNNNNNNNNN NNNNNNNNNN NNNNNNNNNN NNNNNNNNNN NNNNNNNNNN
11451 NNNNNNNNNN NNNNNNNNNN NNNNNNNNNN NNNNNNNNNN NNNNNNNNNN
```

FIGURE 3E

11501 NNNNNNNNNN NNNNNNNNNN NNNNNNNNNN NNNNNNNNNN NNNNNNNNNN
11551 NNNNNNNNNN NNNNNNNNNN NNNNNNNNNN NNNNNNNNNN NNNNNNNNNN
11601 NNNNNNNNNN NNNNNNNNNN NNNNNNNNNN NNNNNNNNNN NNNNNNNNNN
11651 NNNNNNNNNN NNNNNNNNNN NNNNNNNNNN NNNNNNNNNN NNNNNNNNNN
11701 NNNNNNNNNN NNNNNNNNNN NNNNNNNNNN NNNNNNNNNN NNNNNNNNNN
11751 NNNNNNNNNN NNNNNNNNNN NNNNNNNNNN NNNNNNNNNN NNNNNNNNNN
11801 NNNNNNNNNN NNNNNNNNNN NNNNNNNNNN NNNNNNNNNN NNNNNNNNNN
11851 NNNNNNNNNN NNNNNNNNNN NNNNNNNNNN NNNNNNNNNA CTTTATCAAA
11901 AAATTGATGG GGAGAGTTTG TTGAAGCTCA GAGTGAGGAT GGATGTACAA
11951 CATTTCAAGT GCTTCATATC CAGAAAATCA GTAGTCCTCC ATCTGAGTTG
12001 TAGACACAGG AAAGGAGTTG AAGATGAATG GAGTAGGAAT GTAAAAGCCT
12051 TATCTTTACC CTCCTCAGCT TTAGGTCTTA ACAAGAATGA GCCTCCCTTA
12101 GTCTTTCTTT ATGCCCCTGT CCCTGAATGT TGGTGATGAC ATTGTTTTTC
12151 CTGTATTGAA TACAAAAATA TGGCCAGTAA TTTAGGAATC AAGAGGATAT
12201 AATTCGGAAG TAGACTGTTG TGTTTAGGAG TTTTTCTTTC CATTGTGGAA
12251 TTGAGTAGCA GCGGTATATA TGCTATGTCT GGTAAAATGG GCCATACAGT
12301 AGTCTAAGAC ATGAGGAGAC CTTAAGGAGC TTGGACTTAG TTGAGGTGAC
12351 CAGACTATTT AATCTGCTTA GGTGCCACAG CAAAATACCA TAGAGTAGGT
12401 GGTTTAAACA GCAGACATTT ATGATCTCAT AGGTTTGCAG TCTGGAAGTC
12451 AGGGTGCCAG CGTGGTTGGT TCCCGATCAG GGCTCTCCTC CTGGATTGCC
12501 CGTGTCCTCA CATGGCATAG AGAGAGTATG ACAGCATGAG CAAGCTCTCG
12551 TTTTATCTTC TTATAAGAGC ACTGATCCCA TCATGAGGGC CCCATTCTCA
12601 TGACCTCATC TAAACCTGAT TATTTTCCAA AGGCCCCATC TCCAAATGCC
12651 ATCACATTGA GAGTTAAGGC TTCAACATAT GAATTGGTG GGGAAACCCA
12701 GACATTTCAA TCCATAATTC AGGCAGATAT TTGGGAAGTA ACACAGTTGA
12751 AGCACTGAAT GCTATATTTC GTACTATCTA AAGAATCTAG GATGTAATAA
12801 ATTTAAGATG CTTCATTGCC AATTAAATTA AGATACAATG CTTTTTTGAT
12851 TACTTAGAAT TTTTTAAAGA GCTCTTTTAG AGTTAGACAT AGATTTTTGT
12901 CATATGTCAC TTGCACATTC AATAAGATGG AAAACACAAG TGAAAAAACA
12951 CATAAGGAAT TGCTAAATTT CACATATTTA GAGTCTGCCT TCTGAATTGT
13001 TTTTGGAGTC AGAGTTGTTA ATACCTGTAA TTTTCCGTTA AACATCCTCT
13051 GTGCCGCCAA GAGAATTGGT GATGTAGCAT TCCTTTCAAG ATCCCAAAAA
13101 AGAATGCGAA GGTTTTGGTG CTGGCCTTCA GCTTTGCAAT TATGCAAAGC
13151 CAGCCTACTT TGACTGCTGC TTAGGGATTC CCCATCTTCT ACTTCCTTCC
13201 CAGTCCATTT GGTTCCTAGA GGGTGAAATG AATGCTCCAG TATCATTTCT
13251 GGGAATTTCT TTCAGGCTGT TGACTGTCAT ATGCAAATGT CATGCTGGCA
13301 GTTTTGTTAT TTTCCCATGT GTAAGCAATG ACAACATCAT AATTGGCTTC
13351 TGTCTGATAG CAATTGTAAG AGGAATCCCA ATTTCTGAAA TGTTACCCAA
13401 AAAAGTGACT TTAATTGACG AAGTATGATG ATGTAGAAGG ATAGGCAAGA
13451 AATGCAAAAG GTAATTTAGA AACGTTTCAT GGGTAAAATG TGACCTATGT
13501 GATCTAGGGC TATAAAGGAT TTCAATAAGC AGAAGCACGA GGTGGGTTGT
13551 TGAAGAAAGC ACTAAATGTT TTTGGATAAA GAATATAATA ATTTGAGAGT
13601 AAAGGGTAGA GGGAGGGTTA TGTAGGTAAG TAGTTGTAAG ATGGGGAAAG
13651 ATTGGGTAGT ATTTAGCATT TATCCTTAAT GTTGACTTCA GTGTAGTTCT
13701 CTTTGTGTGT TTTCTAGTAT AAACTGCATA CATGAAAGTT AAGAATCTTG
13751 TGTTAAGTCC CATATAGGAA GGAAGTAGAT AGGAAAACCA AACTGGAAAA

FIGURE 3F

```
13801 ATGTATGGAG ATGTTGGTGA AATGACAGGA ACGAAAGCAG CTTGTCTGAG
13851 CTTGATCTCT TCACTTCCTC AGTGGTGGTT CTGACCGCTG GTTTGGCTGA
13901 ACTCCACTTA CCAGGGAAAA GGGCATAAAG TAAACAGGGT TTGTGTGGAA
13951 GAAGTGGAGT AGAACAAAGT GGAGAGGATC TCTGTTCATT TAGTGTATCT
14001 GACAGTGTGC TTGTCAAGTC ATAAAACACT TGAGGATGGA AATCTGGAAG
14051 TCATTGTATA CATTTTCTTC TTTCCCTAAC ATCTAGTCAG TTACAGTTTC
14101 TGCCAGTTCT TTTGCTTTTT CCATGTTTTT GGAGGCTGTT CCTCTTCGCT
14151 CCACATGTAG TAAATGCTCT AGTTCATGAC CCATGTCTTA TCTGGACTGC
14201 CATGTCAGCT TCCTAACTCA TCCATTCACA GCACCAGTGA CTGTAAAACA
14251 GCATTAGTGA GGATAAAACA GTGGCTGTCA AACTTTTTTG ACTGTGGCCC
14301 CCAGTAAAAA TACACTTTGT ATTGCAACTT ATGTATACTT TATATATGTA
14351 TGAATAATTA AAACAAAAGG TTGATTCAAG AAAAATCTTT ACATTTACCC
14401 TGTGCCATGC AATCTTATAT CTTGTATTCT TTTCTGTTTC ATTTTTTTAA
14451 ATGTGTGCTT GCCATCCACT AAATTGATTC CGGAGTTGGA AAAACACTGA
14501 CCTGACAACT AATATCACCA TGTTATTCCT TAAACTCTCC GATGGCTTCT
14551 TACTATCTTC ATGATAAATT TGAAGCCCTC AACATCAGCA TACCAGAACC
14601 TTCATGACCT AACCCTTACC TAGTTATTCT AATCTATTAT TTACCTGATC
14651 CACTCAGCTC ACATTTCATT CCAATAGACA AGTAAAGTTT TTTGTAATTC
14701 CTTGTAGCTT GCCTTTCTTC ATGGTGTCCA CTCTGTTGAA AATCTACTAC
14751 CCTCCATTTC TTCAGTGCTT TACTGCTTAC TCCTACCCAT TCCTGGGGCT
14801 CAAGTCAGGC CCCTATAACC AGGATGCTTT TCCTAACACT CCTTGCCCTA
14851 CCACCAGGCT GGGTTAGGTA GTTCTCCATT ATATAATGTG GTTCTCAATG
14901 TTGTTACCTG TTTATTATTA TGTGTTTTTC TCTTATTGTC CCATAAAATA
14951 GTGAATATTC GAGAGGATAA GGAAGTCTCC CATTAAGCAT CCCTAATGTT
15001 TAGTATGTAA CATGTTGGCA TTGGTTGGAT GAATGAGAAA AAAAAAAGAT
15051 TCTTCTGTTT GGAAGGAAGA TACAACTGGT ATCCCTTAAG TCTTTTCTTT
15101 TTTTTTTTTT TTTTCCTTTC TCTATAGACA AGGTCTCACC ATCACCCAGG
15151 CTGGAGTGCA GTGGTGCAAT CACAGCTCAC TACACCCTTG TACTCCTGGG
15201 CTCAAGTGAT CCTGCTACCT CAGCCTCCCT AGTAGCTGGG ACTGCAGGCA
15251 TGCACCACCA TGCTCAGCTC ATTTTAAAAA AATTTTTTTT GTTGAGACAG
15301 AGTCTTGCTA TGTTGCCTAG GCTGGTCTTG AACTCCTGGG CTCAAGTGAT
15351 CCTCCTGCCT CAGCCTCCCA GAGTGCTAGG ATTATAGGCA TGATCCACTG
15401 CACCTGGCCC CTTAAGACCT TTAATTGCAG AGCAGCAGAG GACAAATGAC
15451 ATAAATACAG GATTTGACTT TCATTTTTAA GTATCAAATT AGTGATGGGT
15501 TGACAAACAA GTCATACAGA ATGTTCATGA ATCAGTTCGG CCCAGGTAAC
15551 TCATAACCCA AGACCTTTGG GTCAATGAAA TTCTGCCACC TAAGTAGCAC
15601 CATCCAATGA TGTCATACCT AAAAAGGAAA TTGAGTTGTA GAATTTTAGG
15651 TTTTAGGATT CTTTCTCTAA AACTGAGGAG CTGTGCCACT CTTCAAAGCC
15701 TCACAATTAC ATTTCATTGG TTCTTATGCC ATCTGGGTTC TGGTTAGAGG
15751 GCTGATGGAA GTACTCAAGA AATATTGGAA GTACTCAAGA AATATTAGAA
15801 GGTGGGAAGA AGGTACCTCT CTTGTTCTTG TCAGTGGCAG CACCAACAGT
15851 GGGACTTTGG GTCTCTGGGT TCCAGCTCAG CAGCAGAGGT ACTAGTACTG
15901 TAGCTCCAGC AGCTTCAGCA GGAGTGCAGG CTCATGGGAT CAGAGAACCA
15951 CCTTTTCCGC TTGTTCTTC CAGCCCAGCC AACAAGTTTG TAGCTATTTC
16001 CCTGCATTAA AACTCCCCTC TGTTTGAAAT ATCTATAGTA ATTTTTCTTT
16051 TCCTGACTAA TACAACCTGT TAAAGAAGCT GAAGCTCTGG TAAGTTAAAT
```

FIGURE 3G

16101 GCCCAACAAT GGTCTTGAGT AGCTAGTGAT TTTTGTTGCT ATTGGTAAGT
16151 AAATCTAGAC ACTACTTTTT AGTCCCTTTT TTAAAAGAGG ACTGGTTTAT
16201 CTATGATGAA TACATGATTG ATTGATTGAT TGATTGATTG ATTTTTACTT
16251 TTTCTTTTTT TTTTTTTGAG ACGGAGTCTT GCTCTGTCAC CCAGGCTGGA
16301 GTGCAGTAAC ATGATCTCTG CTCACTGCAA GCTCCTCCTC CCGGGTTCAC
16351 GCCATTCTCC TGCCTCAGCC TCCTGAGTAG CTGGGACTAC AGGCATCTGC
16401 CACCACGCCC GGCTAATTTT TTTGTATTTT TGTAGAGAC GGGGTTTCAC
16451 CATGTTAGCC AGGATGGTCT CGATCTCCTG ACCTTGTGAT CCGCCTGCCT
16501 CAGCCTCCCA AAGTGCTGAG ATTACAGGCA TGAGCCACCA CGCCCGGCCT
16551 AATTTATTAA AACTTTCGGG TGGTCAGGTA ATTCTGATTT GTCAGCCATA
16601 TTTCTAAATT ATCAATNNNN NNNNNNNNNN NNNNNNNNNN NNNNNNNNNN
16651 NNNNNNNNNN NNNNNNNNNN NNNNNNNNNN NNNNNNNNNN NNNNNNNNNN
16701 NNNNNNNNNN NNNNNNNNNN NNNNNNNNNN NNNNNNNNNN NNNNNNNNNN
16751 NNNNNNNNNN NNNNNNNNNN NNNNNNNNNN NNNNNNNNNN NNNNNNNNNN
16801 NNNNNNNNNN NNNNNNNNNN NNNNNNNNNN NNNNNNNNNN NNNNNNNNNN
16851 NNNNNNNNNN NNNNNNNNNN NNNNNNNNNN NNNNNNNNNN NNNNNNNNNN
16901 NNNNNNNNNN NNNNNNNNNN NNNNNNNNNN NNNNNNNNNN NNNNNNNNNN
16951 NNNNNNNNNN NNNNNNNNNN NNNNNNNNNN NNNNNNNNNN NNNNNNNNNN
17001 NNNNNNNNNN NNNNNNNNNN NNNNNNNNNN NNNNNNNNNN NNNNNNNNNN
17051 NNNNNNNNNN NNNNNNNNNN NNNNNNNNNN NNNNNNNNNN NNNNNNNNNN
17101 NNNNNNNNNN NNNNNNNNNN NNNNNNNNNN NNNNNNNNNN NNNNNNNNNN
17151 NNNNNNNNNN NNNNNNNNNN NNNNNNNNNN NNNNNNNNNN NNNNNNNNNN
17201 NNNNNNNNNN NNNNNNNNNN NNNNNNNNNN NNNNNNNNNN NNNNNNNNNN
17251 NNNNNNNNNN NNNNNNNNNN NNNNNNNNNN NNNNNNNNNN NNNNNNNNNN
17301 NNNNNNNNNN NNNNNNNNNN NNNNNNNNNN NNNNNNNNNN NNNNNNNNNN
17351 NNNNNNNNNN NNNNNNNNNN NNNNNNNNNN NNNNNNNNNN NNNNNNNNNN
17401 NNNNNNNNNN NNNNNNNNNN NNNNNNNNNN NNNNNNNNNN NNNNNNNNNN
17451 NNNNNNNNNN NNNNNNNNNN NNNNNNNNNN NNNNNNNNNN NNNNNNNNNN
17501 NNNNNNNNNN NNNNNNNNNN NNNNNNNNNN NNNNNNNNNN NNNNNNNNNN
17551 NNNNNNNNNN NNNNNNNNNN NNNNNNNNNN NNNNNNNNNN NNNNNNNNNN
17601 NNNNNNNNNN NNNNNNNNNN NNNNNNNNNN NNNNNNNNNN NNNNNNNNNN
17651 NNNNNNNNNN NNNNNNNNNN NNNNNNNNNN NNNNNNNNNN NNNNNNNNNN
17701 NNNNNNNNNN NNNNNNNNNN NNNNNNNNNN NNNNNNNNNN NNNNNNNNNN
17751 NNNNNNNNNN NNNNNNNNNN NNNNNNNNNN NNNNNNNNNN NNNNNNNNNN
17801 NNNNNNNNNN NNNNNNNNNN NNNNNNNNNN NNNNNNNNNN NNNNNNNNNN
17851 NNNNNNNNNN NNNNNNNNNN NNNNNNNNNN NNNNNNNNNN NNNNNNNNNN
17901 NNNNNNNNNN NNNNNNNNNN NNNNNNNNNN NNNNNNNNNN NNNNNNNNNN
17951 NNNNNNNNNN NNNNNNNNNN NNNNNNNNNN NNNNNNNNNN NNNNNNNNNN
18001 NNNNNNNNNN NNNNNNNNNN NNNNNNNNNN NNNNNNNNNN NNNNNNNNNN
18051 NNNNNNNNNN NNNNNNNNNN NNNNNNNNNN NNNNNNNNNN NNNNNNNNNN
18101 NNNNNNNNNN NNNACAGGCA CACACCACCA TGCCTGGCTA ATTTTTTGTA
18151 TTTTTAGTAA CAGGGTTTCA CCATGTTAGC CAGGCTGGCA TCGAATTCCT
18201 GACCTCAGGT GATCCGCCCC CCTCAACCTC CCAAAGTGCT GGGATTACAG
18251 GCGTAAGCCA CCATGCCTGG CCTGTATTTA ATCTTCATAG CAGTTTTATG
18301 AGGTAGGTGG TGTCATCCCC ACTTTACAGA GAAGTGGGTT AATGTAGGGT
18351 TCAAATGATA AATAGTAACT TGCTGATAGT CACTGGCAAT TTTAATTTGT

```
18401 CTTCAGTGTA GTAGAGTAAC TGTGAACTGT TAGAGTTATC AAACTGACAT
18451 GGAAAGTTGT ATACCAAAGG AGTCTTAGGA CTGTCCATGG ATACTGTTAT
18501 GTATCATTTC ACTTATATTG GCTTCAGCTT GCGATTTCTC TACTGTAAGT
18551 GGTGAGAATT GATCAGATAG TTAAGGAAGG TCCTTAGATA ATGCAGTATA
18601 CTTATTAACA TACAGACATC AAGAAGCAGA AATATATAGA CATCTTCCTT
18651 TTTGGTTCTA ATAGGGCTTC GTGGGACACA TATGCAACAT GCCTATGATT
18701 TTTACAACCC TGATATGCTA TCTGAATATC CTATAGTAGA TGGAAAACTC
18751 TCCATACAGT GCTACCTCAG TGCATTAGAC CGCTGCTATT CTGTCTACTG
18801 CAAAAAGATC CATGCCCAGT GGCAGAAAGG TAAGTTTTAC CCATTTTCCT
18851 TGGTTTTGGT ATGAGTTGAG AGCAGTCTAA TGTACTAGGT ATCTTGGTA
18901 GGCAACTACT TTGTGGGCAT TCTTCATTTA ATATCCTTTT ACCATTAATT
18951 CCTCATTCAC CAAACAACAT TTTCCCATAG TTTCTGGGAA AGTGTAATTT
19001 ACTAGAAGAG GTAAACTTTG GAACTGAGGT GTATCTCTGC AAAAATATTT
19051 AGGTCGGTTT ACCCCTTGTA AGAAAATCAA AGTGGAGAAA AGAAGGTAAG
19101 TTGAATTTTG TTCATCTTTT GAGAGAGGTA TTTTAACAAG GTTTTGGACT
19151 ACAGCTGTGA TTCAGGGAAA GCTAATGAAA ATGAATTACT AAAGTGATCT
19201 TACCCCAAAA ATAATCTTTT TGCACTTGAC CTGTGAATTT GTATTTGTTT
19251 TTTTACTGTT ATCATTAATC TGGAAATTTG TTGAGGCACT GAAAGGACAG
19301 TATTTGAGTT AATGCTATCA TAACACATTA TTACATAAAG TATACTTTTT
19351 CTGTAGTCCA ACTTTGCTTT TTAGACGTTA TGAGAAGGGG TTAAAAATCA
19401 TATTCAATGA CAAATATCAG TGAATTTAGT CGCTCTGGAT AAGAAGCATT
19451 CTTGCAGTAT ATATTAACAG AATAGTGGTT TTCTAACTTT TTTATTAGGA
19501 CCCACAGTAA GAAGTACATG TTACATTGTA TGTGTATGCC AGACTGAAAC
19551 AAAAATGTCA TGACATTACT TACCCTTGCT GCAAGTTATT CAGTTTGCTA
19601 TTTTTCTACT GCATTTGTT TTTTAAAATA CTCTTTTATT TAAAAAAAT
19651 ACTAATCCTG ACCCACTAAA TTGATTATGT AACCTGCTAA TGTGTATGAA
19701 TCTTAAACTT GAAAATTAGT GACATAGTAC ATATTGTTTC ATCTTTGAGT
19751 GTCTTTTTAA ATGTATACTT TAAGGTATAG AGAGGTTTCA TTATACAGTG
19801 TATTTGTGGT TGCTGTTTAA ACATATACAA ATATCCTAGC TTTATTCTAA
19851 AGTCAAACTT TAAAATTTCA TGGCTTATAT GAATTTCATA GTTTCCTTGG
19901 ACTTCTCTTT CAGAGGGAAA TGATAAAGAT TTTACCTTGA ATGATTTTGG
19951 CTTCATGATC TTTCACTCAC CATATTGTAA ACTGGTTCAG AAATCTCTAG
20001 CTCGGATGTT GCTGAATGAC TTCCTTAATG ACCAGAATAG AGATAAAAAT
20051 AGTATCTATA GTGGCCTGGA AGCCTTTGGG TAAGAGGAGC TATTATGAGT
20101 TTTTTCCTTC TATATTAGAG CATTTTTAAT ATCTGTTAAG CTGTTACTTG
20151 TACAGACCTG AGAAATTGAG AGTCAGAAGA ATCTAGAAG TCATCCAGTC
20201 TAATCTGTGT GTCTCAGTCA GTGAAGAATC TAAGTCCAGA GAGGTGGTAG
20251 TTAACATGCA CAAATTCTTT AGACATTTCT ATTCAGATTT TCTGATTTAT
20301 TTCTTTCAGC TCCATTCATG TTGTCACGAT AAAGTAACTG CACAAGGGCC
20351 TATATTCACT ACAGCAGCCT CTTAACTCCT TACCTCTCTC AGCACCCCTG
20401 CCCCCATGCC CTTTTCCATC CTGCACACTG CCACAGCTAA AGTCAGCTTT
20451 TGTACTCCAC CTGTCTTTTT CTCACTTTAG GCTCCCTAGC ATGCTATGTG
20501 TGTTCAACTC GTTCTGTTTC TCCCTGTGTC TCTTGTGTGT CCTTTCTCTA
20551 TCTGATAAAA TTATACTTGA CTTTTAAAAC TTGGCTCCTG TAATACCATG
20601 ACTTTTCTAA CTAAATAAAC ATTATTATGG ACTTGAAATA GTATTCTATT
20651 CAGTTGATGA ATATTCAGTT GATTGAATAT TCTATTCATT GAAGCCAATA
```

FIGURE 31

```
20701 TAAGTGAATA TAAATATAAA GCTACAGTGC GTCTTTTAAC CTATTCAAAT
20751 CAAGCAGGCT TAACTTGATT ATGAAAACTT TTGAGAAAAA GAACCATATA
20801 TATACAACTG TTATGATTTC TATAGCAATT AGATTGCTGC TACTTGGCTT
20851 TTAATAAATG AGAAAACAAT TATATACACT TAAAGATTTG AATCCTAATT
20901 AGGCCTGCTG TTTAGTGTAA TAAAAACATA GGCTTTAAAC ACTGTAAAAC
20951 TGTAAAATAA ATCTTTCAGG GATGTTAAAT TAGAAGACAC CTACTTTGAT
21001 AGAGATGTGG AGAAGGCATT TATGAAGGCT AGCTCTGAAC TCTTCAGTCA
21051 GAAAACAAAG GCATCTTTAC TGTATCAAA TCAAAATGA AATATGTACA
21101 CATCTTCAGT ATATGGTTCC CTTGCATCTG TTCTAGCACA GTAAGTATAA
21151 ATTTCACCTA CTACTTAACT CCCCTTATTT GGGAGATGTT AGATTTCTAA
21201 GACCAAATCT AGTGTCAAGC ATGTTGGTGG TAGATCACAG AAAATTTTAT
21251 CTTGAGGCTC TCTAATCTGC TATTGTCCAT TGACTTGAAA GATGTATGG
21301 TTGAGGCTAC AGTTCTTCCA GAAGTATTTG TTAATTTCAT ACTGGCTTTC
21351 CTGGCTTCTG TTTTCATGGT TTTTTAATTC TTGACCTACA GTTGAACCAT
21401 AAATACCTGG TTGATGAAGT AACTTGTTTT GTGGCATGAC TTTCACAAGC
21451 TCTGTCATTC CCCACAAGAT GAAAACTCAC ATGCTGCAAT ATTAAAACTA
21501 AGTATATTC CCTACTGCAA TATTAACACT TTGAGTTAGA TCCTTAAAAC
21551 TTTAAGTTAG ATTCTACTTT TACTTATAGC CTAAATTTT ATTGCTACTT
21601 TTATAGCTTC CCACACGCTG TAGCTTTGGA TCAGTTAAAC TTCTGAACTA
21651 TTGTTACACC CTACATAGGT ACTCACCTCA GCAATTAGCA GGGAAGAGAA
21701 TTGGAGTGTT TTCTTATGGT TCTGGTTTGG CTGCCACTCT GTACTCTCTT
21751 AAAGTCACAC AAGATGCTAC ACCGGGTAAG TGCTGAATCT TTCAACAAGA
21801 ATGTATTGAG AACTGAGTCC AGGCACAGTG GCTCACACCC GTAATCCCAG
21851 CAGTTTGGGA GGCTGAGGCG GGCAGATCAC CTGAGGTCAG GAGTTCGAGA
21901 CCAGTCTGGC TAACATGGCT GAAACCCCAT CTCTACTAAA AATACAAAAA
21951 TTAGCCAGGT GAGGTGGTGC ATGCCTGTAG TCCTAGCTAC TTGGGAGGCT
22001 GAAGTACGAG AATCACTTGA ATCCAGGAGA GGAGGTTGT GGTGAGCCAA
22051 GATCACACCA CTGTGCTCCA GCCTGGGTGA CAGAGCGAGA CTCTGTCAAA
22101 AAAAAAAAA AAAAATGTAT TGAGAACTAC TCTGGGGAAG TTGATTTAGC
22151 AGTCTTCTCA AGTGAGCACC TGAATCTGTC CCACAGATCA TTACAATATT
22201 TTAGTCTTCA TTACTTCTTT CAGTAGGTTT TTACTCTCTG CCCTAAAAAT
22251 CTATCCAAAA AAAAAAAAAA ATTCTACCTT ATCTGGATAA AGGATAGGAC
22301 TAAGTTATCT AATTTTTATA GGCTTATGGT CTTGGCTATA TTTAAGGTCA
22351 CTTTTGTGCT TTCCCTGAGC AGGAAAGAGC AAAAATGTAG AGATAAACTG
22401 ATGAAAACTT GACATTACTT TTTAAAATTA TACCATGGGC CAGGTGCAAT
22451 GGCTCACACC TATAATCCCA ACACTTCACG AGGCTGAGGT GGGAGGATTG
22501 CTTGAGGCCA GATGTTCAAG GCCAACCTGA GCAACATAGT GAGACCCCAT
22551 CTCTATAAAA AATAATAAAA ATAAAATAAT TATACCATGG ATTAATTGTA
22601 GACAAGTTAT TTATAGTTTC AAATTATGCC TGTTTCCTAA CTTGTCTAGT
22651 GGCAGATACT CAATAATAGA TTTCTAGTCT GACATCATAG GAGATTTGTC
22701 AAATAGGTAT CATCTTATCT TTTAACTAAT CAGTAGCCAG TAGTTTTAAT
22751 GAAAATGAAA AGTTGTTTTG CCTCATTTGG CAACATTTTA CTTAGGCTTC
22801 TTTGGACAT GATTTTTCAA AAAAATCTTT TAATGTTGAA TTATTCACTA
22851 TTTTAGGGTC TGCTCTTGAT AAAAATAACAG CAAGTTTATG TGATCTTAAA
22901 TCAAGCCTTG ATTCAAGAAC TGGTGTGGCA CCACATGTCT TCCTGAAAA
22951 CATGAAGCTC AGACAGGACA CCCATCATTT GGGTAAAAAT ATTAAATGTT
```

FIGURE 3J

```
23001 CTTTAAGTTA ACCCATTTGG AGGGCTGATA TCATTAAGGA TGCTACATAT
23051 ACGATAAGGA TATCAAGACT TTACTCAGTA CTAATCTGAT GTCAGTGAAA
23101 ATTATTGGGA TATATGAAAC TTATCTTTAG CTTTATTACC AGATGAATTG
23151 TATATCATAA CTAATTGTAG ATATTCTCTC CCTTTCCTTT AGTCAACTAT
23201 ATTCCCCAGG GTTCAATAGA TTCACTCTTT GAAGGAACGT GGTACTTAGT
23251 TAGGGTGGAT GAAAAGCACA GAAGAACTTA CGCTCGGCGT CCCACTCCAA
23301 ATGATGACAC TTTGGATGAA GGAGTAGGAC TTGTGCATTC AAACATACCA
23351 ACTGAGGTAA ATAAAAGAGT TCCCATCTCC ATATCTTAGG GTTAGGAGA
23401 CCTAACTGGG ATTTAGCAAC ATAAATAAAT GTCAGTAAAG AAGAGTAAGG
23451 GCTCTGGGAG TAGATTCTAG CTGTACTATT TCCAATTGTA TAAAGTGCTT
23501 TGCATTTGAA TTATTAATAT TTTAAGAATA TACAGTAAAG GCCGGGTGCG
23551 GTGGCTCACG CCTGTAATCC CAGCACTTTG GGAGACTGAG GCAGGCAGAT
23601 CACGAGGTCA GGAGATCAAG ACCATCCTGT CCAACATGGT GAAACCCTGT
23651 CTCTACTAAA AATACAAAAA TTAGTTGGGC TTGGTGGCAC GTGCCTGTAA
23701 TTCCAGCTAC TCAGGAGGCT GAGTCAGGAG AATGGCTTGA ACCAGGGAGT
23751 CAGAGGTTGC AGTAAGCTGA GATCACACCA CTGCACTCCA GCCTGGCGAC
23801 AGAGCAAGAT TCCATCTCAA AAAAAAAAAA AAAAAAAAAA AAGAATATAC
23851 AGTAAATACT AGGTTTTATT AATGATACCA GGATTTAAAG GAAGACTGAT
23901 ATAGAGAGAA GGTTCATTTG TGGTGTGTGT CTTTGTGAGA GATGGAGTAG
23951 AGGGACAAGG ATCCTTTCAC ATCTCATCCC AGATCATGGT CAAAATCTGT
24001 CCTCAAATTG TCAAGAAGTA ACAATCATAG CTATGATTTG AATTCCTGTT
24051 ACCTGCTAGG CACTTTACTT ACGTTTTCTT ATTTAATCCT TACAACAACC
24101 TCCTTGAAGT TTATAAATGA TACTGTCCTC CCTTTAGAGA TGAGCCTCCA
24151 AGAAGTTACA TTACTTGCCC AGGATTATAG GTAGTAAGTA TTAAAGCCAG
24201 GTTATAAACT AAGGACTTTA TAACCTTGAA ACTACTTATT TATCTGCTTA
24251 CTACAAGTTT GGTAAATGGA TAGTCTTGCT TTTTGCTATT ATACAAATTA
24301 GGTAGCAAGT CAAACCGCCA CTGTTTGAGT TGCAAATACA AGACGTAACA
24351 AGTAAAATAC TGTTACGTGG TGGGTCTCTG TGGCAGGCTT CCTCTCCCCC
24401 CCATATGGAT AATTGTATAC TAAATTCACC ATAAGGTGAA AAATGGATAT
24451 TGAGTTCCCT TCATGAAAAG TTATATAAAA TATATATTTA GCATAAACTT
24501 CTCCAGAGTT GTCCTTTATT AAGTTTCTTT ACAGAAACTT TAATTGGTGC
24551 CATGATTCTT GTGGGGAAA GAATCATAAG AGCCATCAAC TTTTTTCCTT
24601 TCATTTTAGC ATATTCCAAG CCCTGCCAAG AAAGTACCAA GACTCCCTGC
24651 CACAGCAGCA GAACCTGAAG CAGCTGTCAT TAGTAATGGG GAACATTAAG
24701 ATACTCTGTG AGGTGCAAGA CTTCAGGGTG GGGTGGGCAT GGGGTGGGGG
24751 TATGGGAACA GTTGGAGGAA TGGGATATCT GGGGATAATT TTAAACGATT
24801 ACATGTTATG TAAATTTTTA TGTGACTGAC ATGGACCCTG GATGACTATC
24851 GTGTACTTGG GAAAGTCTCT TTGCTCTATT TGCTGACATG CTTCCTGTTG
24901 TGGTCTGCC AATGCCAAAT GTACTGAAT GATGTTAACC CCTCTCTAAA
24951 ACTTCATACC TCTTTGGCCA TTTGTATGCA TGATGTTGG TTTTTAAACA
25001 TGGTATAATG AATTGTGTAC TTCTGTCAGA AGAAGCAGA CGTACTAATC
25051 TCCAATTAAA AAATTTTTTA ACATGTAAGA ATTTGTACT TTGAACAACA
25101 AGATTACAGA AAGTACCTGT GGTTTTTGGA AAACATTCT AGCTTGCCGA
25151 ATGTGACAAC ATTCCCCAGT GTGGTAAAAT TGGGGTAAAA TGTGGTAAAA
25201 TGTGATACGC ACAAACCCTT TGAAAATAGC AAAACAAACA TGCCCTTTTT
25251 CTAAAATTGA TAAATCCTAA AGAGGAAGAA AAGAGCTGGG ACAATAAAAC
```

FIGURE 3K

```
25301 ACTGGCTCTG GAATCTGGAA TGTTAAGTCC AGGCCAGCAG TGACAAAAGT
25351 TATTGTAATG ACCTCTGAAC AGAGAAACAC TGCCATTGAA GAGGCTTCTG
25401 GTATAGAAAA CATGGTACAT TCAGGAGCTG TGAATATAGC TCTAGGTGTG
25451 CTCCTGAATC AGTTCATGGT AGATTATCCT GAACAACAGT GAGATGTTAT
25501 TGGAGGTGTG GATGAGGGAG TTTGTTGTTG CAGTCCTTCT TTGCACCTTA
25551 TTTTAAAGAA TAAATGAAAC ATTTTTCTGG TTACTTTTTT AAAAATTTAA
25601 AATGGAAGGG AAGAATAGGG GCAGGGCATT ATTAGGCTAT TTCTGATGCT
25651 TCAGTGTTAT AAATTCAACA TAGAGGCTGA CAACCTAAAT TCATGGTGTA
25701 ACACAGCTCT TTTCCTTTTC CTTTTTTTTT TTTTTTTGGT ATCTGTTCAA
25751 TGAAAATAAG GTATGACCCA AGTTTTTACC TAGTCTGACT AGAAGTACTC
25801 CACTTCAAGG TCTGAAGTAG GACTTTTACC TTAAAAAACA ACAACAAACA
25851 AAACTATCAC ACAGGATAGA TAAGAAGATT GGTTAAACAG TTTTGTGTAG
25901 ATCTTTTTGG TGCTGAACTA TGACATGACC CTTATAGATT GTAAAATAGG
25951 GATAGTTGGA ACTAATGTAC AGAACTAAAT TTTTTAAACT TTATTTGCTG
26001 TTAAATTCTG TGAAGTTTCA GTTATCTAAA ATAAATATAC ACAAATATGA
26051 AATATAATGT TTCAGATTGC AAGGTAATAT GTAATAGTAG TGTTTGTAAG
26101 ATACTCTGT CTAATATTAA CTAGTAGTAT TTTGATTTGT ACAGTCATAA
26151 TTTGTTAAAA TGACTTCATT TAACATTCAC TGATGTAGAT TAATAATGTA
26201 AGTTCTGATT TAAAGAATGG TGGCAAAATG GTGCATGTAA TACTTTTGCA
26251 AGTGTTGGGG AGATCGGTAT GTTTTGAAAA GAGTAATTTA ACTTTTGGGT
26301 GCCAGGAAAT GGGTTTTCTC AAAGTCCATT GCCGGCAATG GGCAGGCCTG
26351 CAAATACTGG CACAGAGCAT TAATCATACA CCTTATTAAC GGTGAGGTGA
26401 ATAACTTTGA AATAAAGTTT TAGAGAAATG TTTCAGATAC TTGAGTATTC
26451 TTTTTCACTC TTGAACTAAC AACTTCGGCA AGAAATCAGC TAATATTCTA
26501 TTTTTAAATA TGGGCATTAA TTTCATTTCA GTTCGTTCAC TCATTCCATT
26551 CATTTATCAT TTCACAAACA TTTGAAATCC TAATATAAGC AAGGTGCTCT
26601 GTTTAAGGCA GAAATTTGAA AATGTACAAG ATATATGGTC TTGTCTTTAA
26651 GGACCTGTTC ATCTAGAATG GAGGAATTTA CACTGATAAT TATTCCTACA
26701 CTTGAAACAA AGAAATTAAC TCTCAAATTG CGTGGCAAGC ATATATAGAC
26751 TTTGCTATAA ATATTTATGA AATGAGTTAC TGTTTTCCTT AAAAAAGCTA
26801 AGACTAACGG CTGGCAATCA AATAAGAGCA AATTTAGTGG TGAACGTAGA
26851 ACTGCCCACT ACCAGCTAGA GTCTCCAACC TAAAGTCCC ATGTTGCTAG
26901 TGATCCCCAG GGGTTTTATA GAAGGAATCC CTGCATTGGC AGTAATTTG
26951 GATTAGATGA TCCCTAAGAG CACCATCAAG TCTTAGGATT CTATGAATTA
27001 GGAAATAAAC CAAATTATAT ATTTTCTAAT ACTGATCAGC TCATATTTA
27051 TCATCATGTC ATGTCTGGCT TTCATACTGG GAATACAGAT ATAGAAGGAA
27101 TCGACACAAC TAATGCATGC TATGGAGGCA CAGCTGCTGT CTTCAATGCT
27151 GTTAACTGGA TTGAGTCCAG CTCTTGGGAT GGTATGTTAC ATGCCTATTC
27201 CCCGCCGTCC CCCAAAATTT TTTCTAAGG TTCAATAGAC CCAAATGACA
27251 CTTTAATTAA TGCAATACGC AAACTTTTGT AATTTATCCT TGTTTGGATA
27301 TATTAAGAAA GATATTTTAC CTGTCTGTCA TTATCCGAAT TGTGAATTGG
27351 TTATCTTATC TTGTAGGACA AATGGTCTAT TCAAATTTA GTCAGATCGA
27401 TGACAGAGCC TTGGCAGATG AATTTTAAAA AAAATTAGA GCATTTTCTT
27451 TCTTTATCAA AGAAGGGAAA AGCATATTCT GGGAAAATA TAACAGACTT
27501 CAGTTTCCAT GTTTGGTTAT AGTGTTGAAT TCCTTCTTGT GAATAACAA
27551 AAAATATTTT TCAGGACGGT ATGCCCTGGT AGTTGCAGGA GATATTGCTC
```

FIGURE 3L

27601 TATATGCCAC AGGAAATGCT AGACCTACAG GTGGAGTTCG AGCAGTAGCT
27651 CTGCTAATTG GGCCAAATGC TCCTTTAATT TTTGAACGAG GTAAGTGCTT
27701 GGGAAAGCAT TTTTGTTTTT TTTAGCACAA TATGCTGAGA AATTTGAAAA
27751 TAGAAGTAGG AGCTGTCGCT TACTTAATGG TCATTAAATG CAGGTACTAC
27801 TTGCTAAGAG CTTTATGTGT GTTATCATAT TTATGTTTTT TTTTCTTTTT
27851 TTTTTTTTTT GAGACGGAGT TTCACTCTTG TTGCCCAAGC TGGAGTGCAA
27901 TGGCACGATC TCGGCTCACT GCAACCTCTG CCCCCAGGTT CAAGTGATTC
27951 TCCTGCCTCA GCCTCCTGAG TAGCTGGGAT TACAGGCACA CACCACCATG
28001 C (SEQ ID NO:3)

FEATURES:
Exon: 16553-16577
Intron: 16578-18664
Exon: 18665-18829
Intron: 18830-19913
Exon: 19914-20079
Intron: 20080-20969
Exon: 20970-21140
Intron: 21141-21668
Exon: 21669-21775
Intron: 21776-22856
Exon: 22857-22982
Intron: 22983-23192
Exon: 23193-23356
Intron: 23357-24609
Exon: 24610-24696

CHROMOSOME MAP POSITION:
Chromosome 5

ALLELIC VARIANTS (SNPs):

| DNA Position | Major | Minor | Domain | Protein Position | Major | Minor |
|---|---|---|---|---|---|---|
| 2061 | G | A | Beyond ORF(5') | | | |
| 3388 | C | T | Beyond ORF(5') | | | |
| 4147 | - | T | Beyond ORF(5') | | | |
| 12272 | G | A | Beyond ORF(5') | | | |
| 12936 | A | C | Beyond ORF(5') | | | |
| 13560 | C | A | Beyond ORF(5') | | | |
| 14127 | T | G | Beyond ORF(5') | | | |
| 18789 | T | C | Exon | 50 | G | G |
| 18901 | A | G | Intron | | | |
| 22095 | G | A | Intron | | | |

FIGURE 3M

| 22257 | - | A | Intron |
| 22582 | A | G | Intron |
| 25232 | A | T | Beyond ORF(3') |
| 26224 | C | G | Beyond ORF(3') |
| 26695 | C | T | Beyond ORF(3') |
| 27982 | A | G | Beyond ORF(3') |

Context:

DNA
Position

2061　CGTATCTCGCAGCTCCGTCATTGGCAACTGGGCTCTCGTGCCACCTCACGTCAGTCTCTC
　　　ACACCACTTCCTCGGCCCTGAGACTTTGTCCCCGCCTCTTCTCCCCGCCCTTCCAGCCAC
　　　GACGGAAAATCCTAGCGAGTCATCGCCTCTAGTTTCCTTTTGATTGGTAGAAGCCCGACT
　　　GGGGGCGGCGCTGCCGGGCAACTCTACCGGCCGCGATTGGCTGTGGGAGCCACCGTCC
　　　CGCCTCCCAGCGACTCTCGGCGGTGCCGGAGTCGGGTGGGTTGGCGGCTATAAAGCTGGT
　　　[G,A]
　　　GCGAAGGGGAGGCGCCGCGGACTGTCCTTTCGTGGCTCACTCCCTTTCCTCTGCTGCCGC
　　　TCGGTCACGCTTGGTGAGTGTCCCGCGCTGGGGAGTAGAACTGGGCTGCCGGAGGTGCCGC
　　　GGGCGGGTGTGGCCAGACAGAGGCGGTGTCCTTGACTAGGCCGAAGGAGCTGGGGCT
　　　CTGGGTCAGGACGTAGGCGTGGACTTTGCCCGGGAGGATGGGGCACCGTGAGCGGGGCCG
　　　CGCCGCGGTTCCCTCGTGAGGGACCTGAGGCCGACCGTAGCGGATCTGAGAAGATCCGAG

3388　CCTATGGCCTTAGCCTTAAGGCATCAGTAGCTGCTTTCACTGCTCACCTCTGCTGCAGCT
　　　CCCACCTTCCCGAGGATGCTCTTGCCACCTGCTGCAGTAGGATGATGTGTTCTGGTTGC
　　　TGCTAACTAACATTTGCTCTGTTTTAGGCATGAATATGAAAAACAATGACAAGATAAACA
　　　ACAAAATTAAGACAAATGGAAGTGCTCCTAGAGTTAACAGATTTTTCCTTCTGAGATGTG
　　　TTTGGACTTTATTGCACAGATACTATTAGATGAGAGGCAGTTGAAAGTCGTTAACATTA
　　　[C,T]
　　　CCGTGTCAGTAGTTCTTTGCACTTGAGACACCTAAGCAGCTTGTGTTCTTTAAACTTTAT
　　　TTAAAATTGCAGTTATTTTTGTGTGAAGAAGGGGGCAGGGATAGCATACCTTATCGGAA
　　　GAGAGAAAGGCTTTCTTTGTGTCTACCTTTGTAGATATTTCTCACCTAAGTTTGTAAGTT
　　　TGCCCTTTATTCGGTTCTACTTTAGTTCAGCTCAATTCTAGTATAATCATCAGTAACCCC
　　　AGCACTCAGAAGGTCTGACTTACCGCTGTGGGAGGGAGTGTAAAAGGATATTTTATGTTT

4147　AAAACCCGATATTGTTGTAACATCAGTTTCCTGTGTCCTCTAGAATCATTTAAAACCTGG
　　　TTGGATCTTCCATAATCCAGTGGAATTGGATATGAGATGTAGCTGGAGAAGTTTGTTTTG
　　　CTACATATCAGAATCTCCAATTAGTTTCATTTAGAAAGGAATATAGCCTTATAATTTTAT
　　　GCTGGGTTACTGTGGAACCAAATATCATAGAAGGATGTGTGATATTTTTATGTTTTCAA
　　　GAAGGTAGTATAGATTTAAAAGGTGGGATACATATTACCTGTCCTAATGATAGGACTAGA
　　　[-,T]
　　　TTTTTTTTTTTTTTTTTTGGGGAGACAGAATCTCGCTCTGTCGCCCAAGCTGGAGTGCA
　　　GCAGCGTGATCTCGGCTCACTGCAACTTATGCCTCCCAGTGATTCTCCTGCCTCAGCCTC
　　　CCAAGTAGCTGGGACTACCGGCATGTGCCACCACACCCAGCTAATTTTTTGTATTTTTA
　　　GAAGAGATGGGGTGTCACCATGTTGGTCAGACTGGTCTTGAACTCCTGACCTCAAATGAT
　　　CCGTCCGCCTTGGCCTCCCAAAGTGCTGGAGATTACAGGCGTGAGCCACCATGCCTGGCTA

12272   AGAAAATCAGTAGTCCTCCATCTGAGTTGTAGACACAGGAAAGGAGTTGAAGATGAATGG
        AGTAGGAATGTAAAAGCCTTATCTTTACCCTCCTCAGCTTTAGGTCTTAACAAGAATGAG
        CCTCCCTTAGTCTTTCTTTATGCCCCTGTCCCTGAATGTTGGTGATGACATTGTTTTTCC
        TGTATTGAATACAAAAATATGGCCAGTAATTTAGGAATCAAGAGGATATAATTCGGAAGT
        AGACTGTTGTGTTTAGGAGTTTTTCTTTCCATTGTGGAATTGAGTAGCAGCGGTATATAT
        [G,A]
        CTATGTCTGGTAAAATGGGCCATACAGTAGTCTAAGACATGAGGAGACCTTAAGGAGCTT
        GGACTTAGTTGAGGTGACCAGACTATTTAATCTGCTTAGGTGCCACAGCAAAATACCATA
        GAGTAGGTGGTTTAAACAGCAGACATTTATCATCTCATAGGTTTGCAGTCTGGAAGTCAG
        GGTGCCAGCGTGGTTGGTTCCCGATCAGGGCTCTCCTCCTGGATTGCCCGTGTCCTCACA
        TGGCATAGAGAGTATGACAGCATGAGCAAGCTCTCGTTTTATCTTCTTATAAGACCAC

12936   CCATCTCCAAATGCCATCACATTGAGAGTTAAGGCTTCAACATATGAATTTGGTGGGGAA
        ACCCAGACATTTCAATCCATAATTCAGGCAGATATTTGGGAAGTAACACAGTTGAAGCAC
        TGAATGCTATATTTCGTACTATCTAAAGAATCTAGGATGTAATAAATTTAAGATGCTTCA
        TTGCCAATTAAATTAAGATACAATGCTTTTTTGATTACTTAGAATTTTTTAAAGAGCTCT
        TTTAGAGTTAGACATAGATTTTTGTCATATGTCACTTGCACATTCAATAAGATGGAAAAC
        [A,C]
        CAAGTGAAAAAACACATAAGGAATTGCTAAATTTCACATATTTAGAGTCTGCCTTCTGAA
        TTGTTTTTGGAGTCAGAGTTGTTAATACCTGTAATTTTCCGTTAAACATCCTCTGTGCCG
        CCAAGACAATTGGTCATGTAGCCATTCCTTTCAAGATCCCAAAAAAGAATCCGAAGGTTTT
        GGTGCTGGCCTTCAGCTTTGCAATTATGCAAAGCCAGCCTACTTTGACTGCTGCTTAGGG
        ATTCCCATCTTCTACTTCCTTCCCAGTCCATTTGGTTCCTAGAGGGTGAAATGAATGCT

13560   TTTCAGGCTGTTGACTGTCATATGCAAATGTCATGCTGGCAGTTTTGTTATTTTCCCATG
        TGTAAGCAATGACAACATCATAATTGGCTTCTGTCTGATAGCAATTGTAAGAGGAATCCC
        AATTTCTGAAATGTTACCCAAAAAAGTGACTTTAATTGACGAAGTATGATGATGTAGAAG
        GATAGGCAAGAAAATGCAAAAGTAATTTAGAAAGGTTTCATGGGTAAAATGTGACCTATG
        TGATCTAGGGCTATAAAGGATTTCAATAAGCAGAAGCACGAGGTGGGTTGTTGAAGAAAG
        [C,A]
        ACTAAATGTTTTTGGATAAAGAATATAATAATTTGAGAGTAAAGGGTAGAGGGAGGGTTA
        TGTAGGTAAGTAGTTGTAAGATGGGGAAAGATTGGGTAGTATTTAGCATTTATCCTTAAT
        GTTGACTTCAGTGTGTAGTTCTCTTTGTGTGTTTTCTAGTATAAACTGCATACATGAAGTT
        AAGAATCTTGTGTTAAGTCCCATATAGGAAGGAAGTAGATAGGAAAACCAAACTGGAAA
        ATGTATGGAGATGTTGGTGAAATGACAGGAACGAAAGCAGCTTGTCTGAGCTTGATCTCT

14127   AGGAACGAAAGCAGCTTGTCTGAGCTTGATCTCTTCACTTCCTCAGTGGTGGTTCTGAGC
        GCTGGTTTGGCTGAACTCCACTTACCAGGGAAAGGGCATAAAGTAAACAGGGTTTGTGT
        GGAAGAAGTGGAGTAGAACAAAGTGGAGAGGATCTCTGTTCATTTAGTGTATCTGACAGT
        GTGCTTGTCAAGTCATAAAACACTTGAGGATGGAAATCTGGAAGTCATTGTATACATTTT
        CTTCTTTCCCTAACATCTAGTCAGTTACAGTTTCTGCCAGTTCTTTTGCTTTTTCCATGT
        [T,G]
        TTTGGAGGCTGTTCCTCTTCGCTCCACATGTAGTAAATGCTCTAGTTCATGACCCATGTC
        TTATCTGGACTGCCATGTCAGCTTCCTAACTCATCCATTCACAGCACCAGTGACTGTAAA
        ACAGCATTAGTGAGGATAAAACAGTGGCTGTCAAACTTTTTTGACTGTGGCCCCAGTAA

FIGURE 30

```
        AAATACACTTTGTATTGCAACTTATGTATACTTTATATATGTATGAATAATTAAAACAAA
        AGGTTGATTCAAGAAAAATCTTTACATTTACCCTGTGCCATGCAATCTTATATCTTGTAT

18789   GGATACTGTTATGTATCATTTCACTTATATTGGCTTCAGCTTGCGATTTCTCTACTGTAA
        GTGGTGAGAATTGATCAGATAGTTAAGGAAGGTCCTTAGATAATGCAGTATACTTATTAA
        CATACAGACATCAAGAAGCAGAAATATATAGACATCTTCCTTTTTGGTTCTAATAGGGCT
        TCGTGGGACACATATGCAACATGCCTATGATTTTTACAAGCCTGATATGCTATCTGAATA
        TCCTATAGTAGATGGAAAACTCTCCATACAGTGCTACCTCAGTGCATTAGACCGCTGCTA
        [T,C]
        TCTGTCTACTGCAAAAGATCCATGCCCAGTGGCAGAAAGGTAAGTTTTACCCATTTTCC
        TTGGTTTTGGTATGAGTTGAGAGCAGTCTAATGTACTAGGTATCTTTGGTAGGCAACTAC
        TTTGTGGGCATTCTTCATTTAATATCCTTTTACCATTAATTCCTCATTCACCAAACAACA
        TTTTCCCATAGTTTCTGGGAAAGTGTAATTTACTAGAAGAGGTAAACTTTGGAACTGAGG
        TGTATCTCTGCAAAAATATTTAGGTCGGTTTACCCCTTGTAAGAAAATCAAAGTGGAGAA

18901   CTTATTAACATACAGACATCAAGAAGCAGAAATATATAGACATCTTCCTTTTTGGTTCTA
        ATAGGGCTTCGTGGGACACATATGCAACATGCCTATGATTTTTACAAGCCTGATATGCTA
        TCTGAATATCCTATAGTAGATGGAAAACTCTCCATACAGTGCTACCTCAGTGCATTAGAC
        CGCTGCTATTCTGTCTACTGCAAAAGATCCATGCCCAGTGGCAGAAAGGTAAGTTTTAC
        CCATTTTCCTTGGTTTTGGTATGAGTTGAGAGCAGTCTAATGTACTAGGTATCTTTGGTA
        [A,G]
        GCAACTACTTTGTGGGCATTCTTCATTTAATATCCTTTTACCATTAATTCCTCATTCACC
        AAACAACATTTTCCCATAGTTTCTGGGAAAGTGTAATTTACTAGAAGAGGTAAACTTTGG
        AACTGAGGTGTATCTCTGCAAAAATATTTAGGTCGGTTTACCCCTTGTAAGAAAATCAAA
        GTGGAGAAAAGAAGGTAAGTTGAATTTTGTTCATCTTTTGAGAGAGGTATTTTAACAAGG
        TTTTGGACTACAGCTGTGATTCAGGGAAAGCTAATGAAAATGAATTACTAAAGTGATCTT

22095   ACAAGAATGTATTGAGAACTGAGTCCAGGCACAGTGGCTCACACCCGTAATCCCAGCAGT
        TTGGGAGGCCGAGGCGGGCAGATCACCTGAGGTCAGGAGTTCGAGACCAGTCTGGCTAAC
        ATGGCTGAAACCCCATCTCTACTAAAAATACAAAAATTAGCCAGGTGACGTGGTGCATGC
        CTGTAGTCCTAGCTACTTGGGAGGCTGAAGTAGGAGAATCACTTGAATCCAGGAGAGGGA
        GGTTGTGGTGAGCCAAGATCACACCACTGTGCTCCAGCCTGGGTGACAGAGCGAGACTCT
        [G,A]
        TCAAAAAAAAAAAAAAAAAATGTATTGAGAACTACTCTGGGAAGTTGATTTAGCAGTCT
        TCTCAAGTGAGCACCTGAATCTGTCCCACAGATCATTACAATATTTTAGTCTTCATTACT
        TCTTTCAGTAGGTTTTTACTCTCTGCCCTAAAAATCTATCCAAAAAAAAAAAAAAAATTCT
        ACCTTATCTGGATAAAGGATAGGACTAAGTTATCTAATTTTTATAGGCTTATGGTCTTGG
        CTATATTTAAGGTCACTTTTGTGCTTTCCCTGAGCAGGAAAGAGCAAAAATGTAGAGATA

22257   AGGTGAGGTGGTGCATGCCTGTAGTCCTAGCTACTTGGGAGGCTGAAGTAGGAGAATCAC
        TTGAATCCAGGAGAGGGAGGTTGTGGTGAGCCAAGATCACACCACTGTGCTCCAGCCTGG
        GTGACAGAGCGAGACTCTGTCAAAAAAAAAAAAAAAAATGTATTGAGAACTACTCTGGG
        GAAGTTGATTTAGCAGTCTTCTCAAGTGAGCACCTGAATCTGTCCCACAGATCATTACAA
        TATTTTAGTCTTCATTACTTCTTTCAGTAGGTTTTACTCTCTGCCCTAAAAATCTATCC
        [-,A]
        AAAAAAAAAAAAAAATTCTACCTTATCTGGATAAAGGATAGGACTAAGTTATCTAATTTTT
```

FIGURE 3P

ATAGGCTTATGGTCTTGGCTATATTTAAGGTCACTTTTGTGCTTTCCCTGAGCAGGAAAG
AGCAAAAATGTAGAGATAAACTGATGAAAACTTGACATTACTTTTTAAAATTATACCATG
GGCCAGGTGCAATGGCTCACACCTATAATCCCAACACTTCAGGAGGCTGAGGTGGGAGGA
TTGCTTGAGGCCAGATGTTCAAGGCCAACCTGAGCAACATAGTGAGACCCCATCTCTATA

22582   TCTGGATAAAGGATAGGACTAAGTTATCTAATTTTTATAGGCTTATGGTCTTGGCTATAT
TTAAGGTCACTTTTGTGCTTTCCCTGAGCAGGAAAGAGCAAAAATGTAGAGATAAACTGA
TGAAAACTTGACATTACTTTTTAAAATTATACCATGGGCCAGGTGCAATGGCTCACACCT
ATAATCCCAACACTTCAGGAGGCTGAGGTGGGAGGATTGCTTGAGGCCAGATGTTCAAGG
CCAACCTGAGCAACATAGTGAGACCCCATCTCTATAAAAAATAATAAAAATAAAATAATT
[A,G]
TACCATGGATTAATTGTAGACAAGTTATTTATAGTTTCAAATTATGCCTGTTTCCTAACT
TGTCTAGTGGCAGATACTCAATAATAGATTTCTAGTCTGACATCATAGGAGATTTGTCAA
ATAGGTATCATCTTATCTTTTAACTAATCAGTAGCCAGTAGTTTTAATGAAAATGAAAAG
TTGTTTTGCCTCATTTGGCAACATTTTACTTAGGCTTCTTTTGGACATGATTTTTCAAAA
AAATCTTTTAATGTTGAATTATTCACTATTTTAGGGTCTGCTCTTGATAAAATAACAGCA

25232   ATGTTAAGGGCTCTGTAAAACTTCATACCTCTTTGGCCATTTGTATGCATGATGTTTGGT
TTTTAAACATGGTATAATGAATTGTGTACTTCTGTCAGAAGAAAGCAGACGGTACTAATCT
CCAATTAAAAAATTTTTTAACATGTAAGAATTTTGTACTTTGAACAACAAGATTACAGAA
AGTACCTGTGGTTTTTGGAAAACATTTCTAGCTTGGGGAATGTGACAACATTCCCCAGTG
TGGTAAAATTGGGGTAAAATGTGGTAAAATGTGATACGCACAAACCCTTTGAAAATAGCA
[A,T]
AACAAACATGCCCTTTTTCTAAAATTGATAAATCCTAAAGAGGAAGAAAAGAGCTGGGAC
AATAAAACACTGGCTCTGGAATCTGGAATGTTAAGTCCAGGCCAGCAGTGACAAAAGTTA
TTGTAATGACCTCTGAACAGAGAAACACTGCCATTGAAGAGGCTTCTGGTATAGAAAACA
TGGTACATTCAGGAGCTGTGAATATAGCTCTAGGTGTGCTCCTGAATCAGTTCATGGTAG
ATTATGCTGAACAACAGTGACATGTTATTGGAGGTGTGGATGAGGGAGTTTGTTGTTGCA

26224   CATGAGCCTTATAGATTGTAAAATAGGGATAGTTGGAACTAATGTACAGAACTAAATTTT
TTAAACTTTATTTGCTGTTAAATTCTGTGAAGTTTCAGTTATCTAAAATAAATACACA
AATATGAAATATAATGTTTCAGATTGCAAGGTAATATGTAATAGTAGTGTTTGTAAGATA
CTCTTGTCTAATATTAACTAGTAGTATTTTGATTTGTACAGTCATAATTTGTTAAAATGA
CTTCATTTAACATTCACTGATGTAGATTAATAATGTAAGTTCTGATTTAAAGAATGGTGG
[C,G]
AAAATGGTGCATGTAATACTTTTGCAAGTGTTGGGGAGATCGGTATGTTTTGAAAGAGT
AATTTAACTTTTGGGTGCCAGGAAATGGGTTTTCTCAAAGTCCATTGCCGGCAATGGGCA
GGCCTGCAAATACTGGCACAGAGCATTAATCATACACCTTATTAACGGTGAGGTGAATAA
CTTTGAAATAAAGTTTTAGAGAAATGTTTCAGATACTTGAGTATTCTTTTTCACTCTTGA
ACTAACAACTTCGGCAAGAAATCAGCTAATATTCTATTTTTAAATATGGGCATTAATTTC

26695   AGGTGAATAACTTTGAAATAAAGTTTTAGAGAAATGTTTCAGATACTTGAGTATTCTTTT
TCACTCTTGAACTAACAACTTCGGCAAGAAATCAGCTAATATTCTATTTTTAAATATGGG
CATTAATTTCATTTCAGTTCGTTCACTCATTCCATTCATTTATCATTTCACAAACATTTG
AAATCCTAATATAAGCAAGGTGCTCTGTTTAAGGCAGAAATTTGAAAATGTACAAGATAT
ATGGTCTTGTCTTTAAGGAGCTGTTCATCTAGAATGGAGGAATTTACACTGATAATTATT

FIGURE 3Q

[C,T]
CTACACTTGAAACAAAGAAATTAACTCTCAAATTGCGTGGCAAGCATATATAGACTTTGC
TATAAATATTTATGAAATGAGTTACTGTTTTCCTTAAAAAAGCTAAGACTAAGGGCTGGC
AATCAAATAAGAGCAAATTTAGTGGTGAACGTAGAACTGCCCACTACCAGCTAGAGTCTC
CAACCTAAAAGTCCCATGTTGCTAGTGATCCCAGGGGTTTTATAGAAGGAATCCCTGCA
TTGGCAGTAATTTTGGATTAGATGATCCCTAAGAGCACCATCAAGTCTTAGGATTCTATG

27982   TTGAACGAGGTAAGTGCTTGGGAAAGCATTTTTGTTTTTTTTAGCACAATATGCTGAGAA
ATTTGAAAATAGAAGTAGGAGCTGTCGCTTACTTAATGGTCATTAAATGCAGGTACTACT
TGCTAAGAGCTTTATGTGTGTTATCATATTTATGTTTTTTTTCTTTTTTTTTTTTTTG
AGACCGAGTTTCACTCTTGTTGCCCAAGCTGGAGTGCAATGGCACGATCTCGGCTCACTG
CAACCTCTGCCCCCAGGTTCAAGTGATTCTCCTGCCTCAGCCTCCTGAGTAGCTGGGATT
[A,G]
CAGGCACACACCACCATGC

FIGURE 3R

ISOLATED NUCLEIC ACID MOLECULES ENCODING HUMAN SYNTHASE PROTEINS, AND USES THEREOF

This application is a divisional of U.S. application Ser. No. 10/193,295 filed on Jul. 12, 2002, now U.S. Pat. No. 6,620,608, which is a divisional of U.S. application Ser. No. 09/819,993 filed on Mar. 29, 2001, now U.S. Pat. No. 6,436,692.

FIELD OF THE INVENTION

The present invention is in the field of enzyme proteins that are related to the synthase enzyme subfamily, recombinant DNA molecules, and protein production. The present invention specifically provides novel peptides and proteins and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the synthase subfamily.

Synthases

The novel human protein, and encoding gene, provided by the present invention is related to the family of synthase enzymes in general, and shows the greatest degree of similarity to human cytoplasmic 3-hydroxy-3-methylglutaryl coenzyme A (HMG-CoA) synthase. Furthermore, the protein of the present invention may be an alternative splice form of the HMG-CoA synthase enzyme provided in Genbank gi4504429 (see the amino acid sequence alignment in FIG. 2). HMG-CoA synthase, along with HMG-CoA reductase which is also found on human chromosome 5, is a transcriptionally regulated enzyme that is important in cholesterologenesis.

Mutation of Csy129 to serine or alanine has been shown to abolish HMG-CoA synthase activity by interrupting the first catalytic step, enzyme acetylation by acetyl coenzyme A, in HMG-CoA synthesis (Rokosz et al., *Arch. Biochem. Biophys.* 312 (1), 1–13 (1994)). A beta-lactone inhibitor compound known as L-659,699, is a strong inhibitor of HMG-CoA synthase (Rokosz et al., *Arch. Biochem. Biophys.* 312 (1), 1–13 (1994)).

For a further review of HMG-CoA synthase, see Mehrabian et al., *J Biol Chem Dec.* 5, 1986;261(34): 16249–55; Ayte et al., *Proc. Nat. Acad. Sci.* 87: 3874–3878, 1990; Gil et al., *Proc. Nat. Acad. Sci.* 84: 1863–1866, 1987; Leonard et al., *Proc. Nat. Acad. Sci.* 83: 2187–2189, 1986; and Russ et al., *Biochim. Biophys. Acta* 1132: 329–331, 1992.

Due to their importance in cholesterologenesis, novel human HMG-CoA synthase proteins/genes, such as provided by the present invention, are valuable as potential targets for the development of therapeutics to treat cholesterol-related diseases/disorders. Furthermore, SNPs in HMG-CoA synthase genes, such as provided by the present invention, are valuable markers for the diagnosis, prognosis, prevention, and/or treatment of cholesterol-related diseases/disorders.

Using the information provided by the present invention, reagents such as probes/primers for detecting the SNPs or the expression of the protein/gene provided herein may be readily developed and, if desired, incorporated into kit formats such as nucleic acid arrays, primer extension reactions coupled with mass spec detection (for SNP detection), or TaqMan PCR assays (Applied Biosystems, Foster City, Calif.).

Enzyme proteins, particularly members of the synthase enzyme subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the synthase enzyme subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the synthase enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract.

DESCRIPTION OF THE FIGURE SHEETS

FIG. 1 provides the nucleotide sequence of a cDNA molecule that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 16 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the synthase enzyme subfamily. Utilizing these sequences, additional genomic sequences were assembled and transcript and/or cDNA sequences were isolated and characterized. Based on this analysis, the present invention provides amino acid sequences of human enzyme peptides and proteins that are related to the synthase enzyme subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the synthase enzyme subfamily and the expression pattern observed. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known synthase family or subfamily of enzyme proteins.

Specific Embodiments

Peptide Molecules

The present invention provides nucleic acid sequences that encode protein molecules that have been identified as being members of the enzyme family of proteins and are related to the synthase enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome 5 (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome 5 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme of the present invention. SNPs were identified at 16 different nucleotide positions. Some of these SNPs that are located outside the ORF and in introns may affect gene transcription.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182:626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in teratocarcinoma and teratocarcinoma neuronal precursor cells, fetal brain, liver adenocarcinoma, lung small cell carinoma, and the genitourinary tract, as indicated by virtual northern blot analysis. In addition, PCR-based tissue screening panels indicate expression in liver. A large percentage of pharmaceutical agents are being developed that modulate the activity of enzyme proteins, particularly members of the synthase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the synthase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in teratocarcinoma and teratocarcinoma neuronal precursor cells, fetal brain, liver adenocarcinoma, lung small cell carinoma, and the genitourinary tract, as indicated by virtual northern blot analysis. In addition, PCR-based tissue screening panels indicate expression in liver.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in teratocarcinoma and teratocarcinoma neuronal precursor cells, fetal brain, liver adenocarcinoma, lung small cell carinoma, and the genitourinary tract, as indicated by virtual northern blot analysis. In addition, PCR-based tissue screening panels indicate expression in liver.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al.(1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-medicated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an. antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in teratocarcinoma and teratocarcinoma neuronal precursor cells, fetal brain, liver adenocarcinoma, lung small cell carinoma, and the genitourinary tract, as indicated by virtual northern blot analysis. In addition, PCR-based tissue screening panels indicate expression in liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof.

The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome 5 (as indicated in FIG. 3), which is supported by multiple lines of evidence, such as STS and BAC map data.

FIG. 3 provides information on SNPs that have been found in the gene encoding the enzyme of the present invention. SNPs were identified at 16 different nucleotide positions. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 16 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome 5 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in teratocarcinoma and teratocarcinoma neuronal precursor cells, fetal brain, liver adenocarcinoma, lung small cell carinoma, and the genitourinary tract, as indicated by virtual northern blot analysis. In addition, PCR-based tissue screening panels indicate expression in liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro. techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in teratocarcinoma and teratocarcinoma neuronal precursor cells, fetal brain, liver adenocarcinoma, lung small cell carinoma, and the genitourinary tract, as indicated by virtual northern blot analysis. In addition, PCR-based tissue screening panels indicate expression in liver.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway.

Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in teratocarcinoma and teratocarcinoma neuronal precursor cells, fetal brain, liver adenocarcinoma, lung small cell carinoma, and the genitourinary tract, as indicated by virtual northern blot analysis. In addition, PCR-based tissue screening panels indicate expression in liver. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in teratocarcinoma and teratocarcinoma neuronal precursor cells, fetal brain, liver and liver adenocarcinoma, lung small cell carinoma, and the genitourinary tract.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme of the present invention. SNPs were identified at 16 different nucleotide positions. Some of these SNPs that are located outside the ORF and in introns may affect gene transcription. The gene encoding the novel enzyme of the present invention is located on a genome component that has been mapped to human chromosome 5 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv.*

*Chromatogr.* 36:127–162 (1996); and Griffin et al. *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme of the present invention. SNPs were identified at 16 different nucleotide positions. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in teratocarcinoma and teratocarcinoma neuronal precursor cells, fetal brain, liver adenocarcinoma, lung small cell carinoma, and the genitourinary tract, as indicated by virtual northern blot analysis. In addition, PCR-based tissue screening panels indicate expression in liver. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al.(1996; *Nat. Biotech.* 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of,the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme of the present invention. SNPs were identified at 16 different nucleotide positions. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from $E.$ $coli,$ the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, $E.$ $coli,$ Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion $E.$ $coli$ expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example $E.$ $coli.$ (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule encoding a hydroxymethylglutaryl-CoA synthase, wherein the nucleotide sequence of said nucleic acid molecule comprises a nucleotide sequence selected from the group consisting of:
   (a) a transcript or cDNA sequence that encodes a polypeptide having an amino acid sequence comprising SEQ ID NO:2;
   (b) SEQ ID NO:1;
   (c) nucleotides 145–1578 of SEQ ID NO:1; and
   (d) a nucleotide sequence that is completely complementary to the nucleotide sequence of (a), (b), or (c).

2. An isolated nucleic acid molecule encoding a hydroxymethylglutaryl-CoA synthase, wherein the nucleic acid molecule has a nucleotide sequence comprising SEQ ID NO:1 or the complete complement thereof.

3. An isolated nucleic acid molecule encoding a hydroxymethylglutaryl-CoA synthase, wherein the nucleic acid molecule has a nucleotide sequence comprising nucleotides 145–1578 of SEQ ID NO:1 or the complete complement thereof.

4. An isolated transcript or cDNA nucleic acid molecule comprising a nucleotide sequence that encodes a hydroxymethylglutaryl-CoA synthase having an amino acid sequence comprising SEQ ID NO:2 or the complete complement of said nucleotide sequence.

5. The isolated nucleic acid molecule of claim 1, further comprising a heterologous nucleotide sequence.

6. The isolated nucleic acid molecule of claim 5, wherein the heterologous nucleotide sequence encodes a heterologous amino acid sequence.

7. A vector comprising the nucleic acid molecule of any one of claims 1–6.

8. An isolated host cell containing the vector of claim 7.

9. A process for producing a polypeptide comprising culturing the host cell of claim 8 under conditions sufficient for the production of said polypeptide, and recovering said polypeptide.

10. The vector of claim 7, wherein said vector is selected from the group consisting of a plasmid, a virus, and a bacteriophage.

11. The vector of claim 7, wherein said nucleic acid molecule is inserted into said vector in proper orientation and correct reading frame such that a polypeptide comprising SEQ ID NO:2 is expressed by a cell transformed with said vector.

12. The vector of claim 11, wherein said isolated nucleic acid molecule is operatively linked to a promoter sequence.

* * * * *

SEQUENCE LISTING

<160> NUMBER OF SEQ ID NOS: 5

<210> SEQ ID NO 1
<211> LENGTH: 2002
<212> TYPE: DNA
<213> ORGANISM: Human

<400> SEQUENCE: 1

```
cgcctcccag cgactctcgg cagtgccgga gtcgggtggg ttggcggcta taaagctggt      60
agcgaagggg aggcgccgcg gactgtcctt tcgtggctca ctcccttcc tctgctgccg      120 ctcggtcacg cttgctcttt caccatgcct ggatcacttc ctttgaatgc agaagcttgc     180
tggccaaaag atgtgggaat tgttgccctt gagatctatt ttccttctca atatgttgat    240
caagcagagt tggaaaaata tgatggtgta gatgctggaa agtataccat tggcttgggc    300
caggccaaga tgggcttctg cacagataga gaagatatta actctctttg catgactgtg    360
gttcagaatc ttatggagag aaataacctt tcctatgatt gcattgggcg gctggaagtt    420
ggaacagaga caatcatcga caaatcaaag tctgtgaaga ctaatttgat gcagctgttt    480
```

```
gaagagtctg ggaatacaga tatagaagga atcgacacaa ctaatgcatg ctatggaggc    540
acagctgctg tcttcaatgc tgttaactgg attgagtcca gctcttggga tgggcttcgt    600
gggacacata tgcaacatgc ctatgatttt tacaagcctg atatgctatc tgaatatcct    660
atagtagatg gaaaactctc catacagtgc tacctcagtg cattagaccg ctgctactct    720
gtctactgca aaaagatcca tgcccagtgg cagaaagagg gaaatgataa agattttacc    780
ttgaatgatt ttggcttcat gatctttcac tcaccatatt gtaaactggt tcagaaatct    840
ctagctcgga tgttgctgaa tgacttcctt aatgaccaga atagagataa aaatagtatc    900
tatagtggcc tggaagcctt tggggatgtt aaattagaag acacctactt tgatagagat    960
gtggagaagg catttatgaa ggctagctct gaactcttca gtcagaaaac aaaggcatct   1020
ttacttgtat caaatcaaaa tggaaatatg tacacatctt cagtatatgg ttcccttgca   1080
tctgttctag cacagtactc acctcagcaa ttagcaggga agagaattgg agtgttttct   1140
tatggttctg gtttggctgc cactctgtac tctcttaaag tcacacaaga tgctacaccg   1200
gggtctgctc ttgataaaat aacagcaagt ttatgtgatc ttaaatcaag gcttgattca   1260
agaactggtg tggcaccaga tgtcttcgct gaaaacatga agctcagaga ggacacccat   1320
catttggtca actatattcc ccagggttca atagattcac tctttgaagg aacgtggtac   1380
ttagttaggg tggatgaaaa gcacagaaga acttacgctc ggcgtccac tccaaatgat   1440 gacactttgg atgaaggagt aggacttgtg cattcaaaca tagcaactga gcatattcca   1500
agccctgcca agaaagtacc aagactccct gccacagcag cagaacctga agcagctgtc   1560
attagtaatg gggaacatta agatactctg tgaggtgcaa gacttcaggg tggggtgggc   1620
atggggtggg ggtatgggaa cagttggagg aatgggatat ctggggataa ttttaaagga   1680
ttacatgtta tgtaaatttt tatgtgactg acatggagcc tggatgacta tcgtgtactt   1740
gggaaagtct ctttgctcta tttgctgaca tgcttcctgt tgtggtctgg ccaatgccaa   1800
atgtactcga atgatgttaa gggctctgta aaacttcata cctctttggc catttgtatg   1860
catgatgttt ggtttttaaa catggtataa tgaattgtgt acttctgtca gaagaaagca   1920
gaggtactaa tctccaatta aaaaattttt taacatgtaa aaaaaaaaaa aaaaaaaaa    1980 aaaaaaaaaa aaaaaaaaaa aa                                            2002
```

<210> SEQ ID NO 2
<211> LENGTH: 478
<212> TYPE: PRT
<213> ORGANISM: Human

<400> SEQUENCE: 2

```
Met Pro Gly Ser Leu Pro Leu Asn Ala Glu Ala Cys Trp Pro Lys Asp
  1               5                  10                  15

Val Gly Ile Val Ala Leu Glu Ile Tyr Phe Pro Ser Gln Tyr Val Asp
             20                  25                  30

Gln Ala Glu Leu Glu Lys Tyr Asp Gly Val Asp Ala Gly Lys Tyr Thr
         35                  40                  45

Ile Gly Leu Gly Gln Ala Lys Met Gly Phe Cys Thr Asp Arg Glu Asp
     50                  55                  60

Ile Asn Ser Leu Cys Met Thr Val Val Gln Leu Met Glu Arg Asn
 65                  70                  75                  80

Asn Leu Ser Tyr Asp Cys Ile Gly Arg Leu Glu Val Gly Thr Glu Thr
                 85                  90                  95
```

```
Ile Ile Asp Lys Ser Lys Ser Val Lys Thr Asn Leu Met Gln Leu Phe
            100                 105                 110

Glu Glu Ser Gly Asn Thr Asp Ile Glu Gly Ile Asp Thr Thr Asn Ala
            115                 120                 125

Cys Tyr Gly Gly Thr Ala Ala Val Phe Asn Ala Val Asn Trp Ile Glu
            130                 135                 140

Ser Ser Ser Trp Asp Gly Leu Arg Gly Thr His Met Gln His Ala Tyr
145                 150                 155                 160

Asp Phe Tyr Lys Pro Asp Met Leu Ser Glu Tyr Pro Ile Val Asp Gly
                165                 170                 175

Lys Leu Ser Ile Gln Cys Tyr Leu Ser Ala Leu Asp Arg Cys Tyr Ser
            180                 185                 190

Val Tyr Cys Lys Lys Ile His Ala Gln Trp Gln Lys Glu Gly Asn Asp
            195                 200                 205

Lys Asp Phe Thr Leu Asn Asp Phe Gly Phe Met Ile Phe His Ser Pro
210                 215                 220

Tyr Cys Lys Leu Val Gln Lys Ser Leu Ala Arg Met Leu Leu Asn Asp
225                 230                 235                 240

Phe Leu Asn Asp Gln Asn Arg Asp Lys Asn Ser Ile Tyr Ser Gly Leu
                245                 250                 255

Glu Ala Phe Gly Asp Val Lys Leu Glu Asp Thr Tyr Phe Asp Arg Asp
            260                 265                 270

Val Glu Lys Ala Phe Met Lys Ala Ser Ser Glu Leu Phe Ser Gln Lys
            275                 280                 285

Thr Lys Ala Ser Leu Leu Val Ser Asn Gln Asn Gly Asn Met Tyr Thr
290                 295                 300

Ser Ser Val Tyr Gly Ser Leu Ala Ser Val Leu Ala Gln Tyr Ser Pro
305                 310                 315                 320

Gln Gln Leu Ala Gly Lys Arg Ile Gly Val Phe Ser Tyr Gly Ser Gly
                325                 330                 335

Leu Ala Ala Thr Leu Tyr Ser Leu Lys Val Thr Gln Asp Ala Thr Pro
            340                 345                 350

Gly Ser Ala Leu Asp Lys Ile Thr Ala Ser Leu Cys Asp Leu Lys Ser
            355                 360                 365

Arg Leu Asp Ser Arg Thr Gly Val Ala Pro Asp Val Phe Ala Glu Asn
370                 375                 380

Met Lys Leu Arg Glu Asp Thr His His Leu Val Asn Tyr Ile Pro Gln
385                 390                 395                 400

Gly Ser Ile Asp Ser Leu Phe Glu Gly Thr Trp Tyr Leu Val Arg Val
                405                 410                 415

Asp Glu Lys His Arg Arg Thr Tyr Ala Arg Arg Pro Thr Pro Asn Asp
            420                 425                 430

Asp Thr Leu Asp Glu Gly Val Gly Leu Val His Ser Asn Ile Ala Thr
            435                 440                 445

Glu His Ile Pro Ser Pro Ala Lys Lys Val Pro Arg Leu Pro Ala Thr
450                 455                 460

Ala Ala Glu Pro Glu Ala Val Ile Ser Asn Gly Glu His
465                 470                 475

<210> SEQ ID NO 3
<211> LENGTH: 28001
<212> TYPE: DNA
<213> ORGANISM: Human
<220> FEATURE:
<221> NAME/KEY: misc_feature
```

<222> LOCATION: (1)...(28001)
<223> OTHER INFORMATION: n = A,T,C or G

<400> SEQUENCE: 3

```
ccattttttcc cgccatcact gtctttaaat tagtccatcg gaattagttt agcctgtgca        60
gtctaacccct agccaataag ggaacgacac agcagtgggg accacgtgcg tcaggaataa       120
gaaccccttt ccctccctcg tccaagtgtg cactcaccat tgctccatct gtaagggtgc       180
accccttctat agaagtacct tgccttgctg agaattaaaa agaaaatttt atattcgact       240
gctatttctt ttgcagcatg gaaactttat ttataacaag atcttctgta tctaattact       300
aaccctttt gttctccatt gcttggcttc ccagtaatca ataatcatgc tcactttgct        360
taattgaaga ttaacgtgat caaaaagacg gtctgttcct tgtagaaatt tccggttgtg       420
taagatggtc attctcatga ccgtctggct aatcatttcc cattatgtac tcctggagtt       480
ggaattattt gcgattccta acgacaaaac tgtatcttct ttcttgtgtt tgtccttact       540
gcctttcagc atattccaat atgccaagaa ttttaatctc ctaccccacc ccaaattgct       600
gttgatcata atcaggcaat gtctctctct ctgtttacta tctagttact ttacatacat       660
atgaagtgag tcatgggcaa tactgtggaa tggaaatcat tactgagtgg tcctcttccc       720
ccaagtcatt tatgccacca cttcacagtg gttccatttc caatatattt tgccactttg       780
ctgctgagaa tgtgtcttac taggttagca tctatagtgg ttaaaagaat ctcccataac       840
aataattgtg tgaatcacag aattaccaat gacccttat caatagcatt cctgttaatt       900
aaattgagat ggggagagat acaaacaact ccgaacctca ctcatggtcc cccaccaaag       960
ctaagtatta tggcttctct ctctgaccag atagaggcag agtttattgc aaagccacaa      1020
gtgtcctcct ttggattccc ccaaatagtg tttcagtgaa ttcctctagc ttgaattgct      1080
cctctctatt tgctggggga gttaggcagt ccgtatccga tggatttact atgccgacaa      1140
ttacgtggcc tttccacagc cttttacttg gcaggtacca catatgaagc ttagaagata      1200
cagtgggcaa caggccaaat ggagtccctt tcctcagagt gcatggcctg gcaaaaatcc      1260
ttgaattcag tatcaacttc ccttcacagg caaggctctg cacccctccc acggatgcct      1320
aatcctgaaa ccatttttgtt ttaggtttag ttagaaagct ttgtctcaag agcacttttg      1380
tttgttctgt tttctttaag tcaaggtagt tttgaataaa ggagacaatn atttgagtat      1440
ttacaaatcg ggtatttaga ctatttacac atatacaagt tctgggtgaa gtattctgct      1500
ccaatttgca atctacgcac actttgctag aaaacgttaa gactgaattc aaatcaagta      1560
cagtatttca gaaatctttc aggtgaagcc tagttctggt tgctaggcaa cctgacagac      1620
tcccaagctg ggaccacctc gcctcccaca tttgaccatc tctccagcgg tgggacgcgg      1680
agtacccatt ggcccgcatc tcctctcact tagtcccaat tggtcggaga acctctcact      1740
ccgctcccgt tggctctcgc cgtatctcgc agctccgtca ttggcaactg ggctctcgtg      1800
ccacctcacg tcagtctctc acaccacttc ctcggccctg agactttgtc cccgcctctt      1860
ctccccgccc ttccagccac gagggaaaat cctagcgagt catcgcctct agtttccttt      1920
tgattggtag aagccggact ggggggcggg cgctgccggg caactctacc ggccgcgatt      1980
ggctgtggga gccaccgtcc cgcctcccag cgactctcgg cggtgccgga gtcgggtggg      2040
ttggcggcta taaagctggt ggcgaagggg aggcgccgcg gactgtcctt tcgtggctca      2100
ctcccttttcc tctgctgccg ctcggtcacg cttggtgagt gtcccgcgct ggggagtaga      2160
actgggctgc ggaggtgccg cgggcggggt gtgggccaga cagaggcggt gtccttgact      2220
```

```
aggcccgaag gagctggggc tctgggtcag gacgtaggcg tggactttgc ccgggaggat   2280
ggggcaccgt gagcggggcc gggcgggggt tccctcgtga gggacctgag gccgaccgta   2340
gcggatctga gaagatccga gaacacaggc gagtcgcgga ggggagaacg cgagagggcg   2400
ttgaggtcta ggtattctaa cgacagagga gttggaggtg ccagagaggc agctgtgacc   2460
gcctagaggt gagtgggggg tgtcaggagg gggagagaag acagttgggc taccaaggcg   2520
tttccagagc gttggttaag ggtggacgcc aaaggatggg caagatcctc tttagacgga   2580
ggctggtagg ttcgcagggg gtgtgtcctg ctgccacata tagagttgat ggaaagaagg   2640
gaagtgggta gcattacttt tcttcctcag ctcaggtgca agaaagcgtt cacaaccgtg   2700
atttagacct ggctaagtac tggggctcag tctgtacttg cttcaaatct catagatcac   2760
tgcctcccgc cttcctgcct ccatattttt ttttgtctac gttttaaaaa ataggcttcc   2820
ttggtgttct gaaatcccac atctctctcc tactaatacc ttcgggacca gctttaggtg   2880
atacagtgta atgggcaggc actcacagag tcctcccaca aataggtttt ggattaagct   2940
aaggatattt caaagcaagt atatggagtc tttgaaaacc cacgtctggc cttgaccagt   3000
ggtagagaaa cgattattct gatccactct ggaggaggga tttggggaac aaataatgtg   3060
aggttgtgcc tgtttgtcat gcttgtccct atggccttag ccttaaggca tcagtagctg   3120 cttttcactgc tcacctctgc tgcagctccc caccttcccg aggatgctct tgccacctgc   3180
tgcagtagga tgatgtgttc tggttgctgc taactaacat ttgctctgtt ttaggcatga   3240
atatgaaaaa caatgacaag ataaacaaca aaattaagac aaatggaagt gctcctagag   3300
ttaacagatt tttccttctg agatgtgttt tggactttat tgcacagata ctattagatg   3360
agaggcagtt gaaagtcgtt aacattaccc gtgtcagtag ttctttgcac ttgagacacc   3420
taagcagctt gtgttcttta aactttattt taaaattgca gttattttg tgtgaagaag    3480 ggggcaggga tagcatacct tatgggaaga gagaaaggct ttctttgtgt ctacctttgt   3540
```

-continued

```
aagaccaaca aatgttttct gattccatat gggcttctta cattttttcac cttggaatct    4680 gggaacaatt gaaacctacc atatgccttg aacagtagca gtaaagagcc agtttctttta   4740 aactagacat tatggtgctg cagctcatct caaaactgat agcaggctac tctggacaca    4800
ctacatatag agtagccctg ctctgcaagg agcagtaata aattaaaaaa aaaattaaaa    4860
agtgatagca gaaagcactt actactgagg gctgctacaa gtattaaatc taaaagattt    4920
gtcctctagt agttataact ccaaattcag ccactgaaaa atgtgacatt tgagtaccct    4980
ttacttcaag gtctcaaagg gatttcaaaa aatcaaaata tatagcccct ctcccaaaag    5040
aagtgtagga atcctgtatg gataagaaga ctgcccataa ctagttttcc atagagagta    5100
ggctatgtag acttgggtat gaatgaccta cctctgtaga agtgcaggtc cctgattaga    5160 aaacttatttt tctgtgtgat ttatcgagga aagcttccag gaagaggtga cttagaacag   5220
ggccttgaag atgagtagaa tctctgatac gcagaccagt aactctggga ggaggcaggg    5280
atgtccatgc ttttttacttg gagaactata ccagagtgta caggtttgag caagtctttc    5340
ttaacattag ttttttacttg cttgctccta aggaggaaag gttgccaact tgttcttaat   5400
ttcctagatt tatctcctgt aacaatgaga aagatcaata ggtaactgtt tatattttat    5460 agtttcacata ccaaaatgtg taggcaatga acttctccaa ccacttcttt gaatcaaggc   5520
taaggaggga gccagaagga agtattcaga acactgagta aactccagaa gaaactacca    5580
ttgcataaat ctggttggcc ctaggcagtc ttatcattct tgtgttttag tctttgccag    5640
actcaaagtg cctatatttc atcccatgag tctgcaaacc tgctttgtgg taacctgcct    5700
ggctacttgc cattcattaa ctgcttcttg acccatgttg attccctctg tcacttactc    5760
tgaaaagacc tgttagaaat aagcttgtga tctgcttgag actttggcaa tactggttta    5820
gccagaatag agaaatcctt aagtagcaca gcaatccttt ctgaatcttc tatttgtttc    5880
ttctttgttc tctgtgtctc tcccacctaa catccctctc caatttaagt aatcaaaata    5940
gaaagagggg cccaggcaag gtggcccacg cctataatcc cagcactttg ggaggccaaa    6000
gtgggtggat tggtttagcc caggagttgg agaacagcct gggaaagatg gcaaaacccc    6060
atctctacaa aaaatacaaa aatcagctgt gtattgtggc atgtgcctgt agtcccagct    6120
acttgcgggg tctgagacag gaggatcact tgagcctggg aggtcgaggt tacagtgagc    6180
agtgactgga atgctactgc attccagtct gggtgacaga gggagaccct gtctcaaaaa    6240
aaaaaaaaaa tttgagggaa tataggcagt gcaaggaaag gcagaatata ggcagttcaa    6300
ggaaaatttc cttgatacaa gtagtgtcaa atgcatatac atacatgaac atcaagaaga    6360
aatattatta tttaagtagt cttaacatgg agaaggaatc ttgtttttca agaactggtc    6420
tctgtggtct gcttaatttg cagaagacaa aggcataatt tgagataata aagaacaaag    6480
ataggttatt ttctcaaagt atgtataatt acagttaatt agagacattt ttggaatatt    6540
gtagtattct ttgcctacaa aactcaagat ctatttctttt ttatggggca gggggggcgta   6600 ggtgggtagt aaacttagtt aatgaagtaa aaggcgctac gactgaagag ctcttaaatt    6660
atgtaattat gtaaaaaaag taaagcttta ttaaatatta ataacatccg aatgtagtta    6720
ccagtgaatc cattaagggc agatgctaaa tttgccagta attaaataga gagcagagga    6780
aatggtgtat gctgtgttaa acatagaagt tgccatctca agtaacaatc agtctttcaa    6840
aacagatgga ctgaagaata tgttccagtc accttcgcaa attatttcta cttaatttac    6900
ataataatgt ttaatgctcc tttgtctaaa tgcttaattt tttaacataa gcagtaagag    6960
```

-continued

| | | | | |
|---|---|---|---|---|
| ggaaaatcac | tttataaaag | gttgggaggg | tgaaggtggc | agtgttgaaa | atgattaggt | 7020 |
| cttgctagaa | aaaataccct | tatttttctt | gaaaaacact | tataagaact | ataagaacta | 7080 |
| aggtaatagt | cagtgtattg | gtgctttgtg | ttacaaagtg | tcttcacata | ttttatcatc | 7140 |
| tcagcaatcc | ttcacaatga | tctggggagg | gcaactgtat | tagcttcatt | ttatagatga | 7200 |
| ggaaactgag | gtccagaatt | gctgccaaag | ccacaatctg | ttacatgcag | tgcaggctct | 7260 |
| tgactgcata | tatctcttta | ctctagaaat | ttgctaactc | attacaactt | gtttatattc | 7320 |
| ctttcccca | attcttgaaa | accttggttt | aaagcctcaa | ttggtgacat | gggcttctta | 7380 |
| tttccttgag | gtttttttgt | ttattccttc | ctgcaatagt | aggcttctta | tatccgttta | 7440 |
| ttaccaggac | tgaacctttc | actataaggg | ctatgaaaat | aagggggaaa | atgttctata | 7500 |
| agctttaagt | atgattttt | ctaagcaaat | gtcaaattct | attctgcata | atgtaattgg | 7560 |
| ataaggaatt | gcttatttta | actcactttg | aattggattc | attagtattt | gaatttgggt | 7620 |
| aggatttata | actttaaaag | cannnnnnnn | nnnnnnnnnn | nnnnnnnnnn | nnnnnnnnnn | 7680 |
| nnnnnnnnnn | nnnnnnnnnn | nnnnnnnnnn | nnnnnnnnnn | nnnnnnnnnn | nnnnnnnnnn | 7740 |
| nnnnnnnnnn | nnnnnnnnnn | nnnnnnnnnn | nnnnnnnnnn | nnnnnnnnnn | nnnnnnnnnn | 7800 |
| nnnnnnnnnn | nnnnnnnnnn | nnnnnnnnnn | nnnnnnnnnn | nnnnnnnnnn | nnnnnnnnnn | 7860 |
| nnnnnnnnnn | nnnnnnnnnn | nnnnnnnnnn | nnnnnnnnnn | nnnnnnnnnn | nnnnnnnnnn | 7920 |
| nnnnnnnnnn | nnnnnnnnnn | nnnnnnnnnn | nnnnnnnnnn | nnnnnnnnnn | nnnnnnnnnn | 7980 |
| nnnnnnnnnn | nnnnnnnnnn | nnnnnnnnnn | nnnnnnnnnn | nnnnnnnnnn | nnnnnnnnnn | 8040 |
| nnnnnnnnnn | nnnnnnnnnn | nnnnnnnnnn | nnnnnnnnnn | nnnnnnnnnn | nnnnnnnnnn | 8100 |
| nnnnnnnnnn | nnnnnnnnnn | nnnnnnnnnn | nnnnnnnnnn | nnnnnnnnnn | nnnnnnnnnn | 8160 |
| nnnnnnnnnn | nnnnnnnnnn | nnnnnnnnnn | nnnnnnnnnn | nnnnnnnnnn | nnnnnnnnnn | 8220 |
| nnnnnnnnnn | nnnnnnnnnn | nnnnnnnnnn | nnnnnnnnnn | nnnnnnnnnn | nnnnnnnnnn | 8280 |
| nnnnnnnnnn | nnnnnnnnnn | nnnnnnnnnn | nnnnnnnnnn | nnnnnnnnnn | nnnnnnnnnn | 8340 |
| nnnnnnnnnn | nnnnnnnnnn | nnnnnnnnnn | nnnnnnnnnn | nnnnnnnnnn | nnnnnnnnnn | 8400 |
| nnnnnnnnnn | nnnnnnnnnn | nnnnnnnnnn | nnnnnnnnnn | nnnnnnnnnn | nnnnnnnnnn | 8460 |
| nnnnnnnnnn | nnnnnnnnnn | nnnnnnnnnn | nnnnnnnnnn | nnnnnnnnnn | nnnnnnnnnn | 8520 |
| nnnnnnnnnn | nnnnnnnnnn | nnnnnnnnnn | nnnnnnnnnn | nnnnnnnnnn | nnnnnnnnnn | 8580 |
| nnnnnnnnnn | nnnnnnnnnn | nnnnnnnnnn | nnnnnnnnnn | nnnnnnnnnn | nnnnnnnnnn | 8640 |
| nnnnnnnnnn | nnnnnnnnnn | nnnnnnnnnn | nnnnnnnnnn | nnnnnnnnnn | nnnnnnnnnn | 8700 |
| nnnnnnnnnn | nnnnnnnnnn | nnnnnnnnnn | nnnnnnnnnn | nnnnnnnnnn | nnnnnnnnnn | 8760 |
| nnnnnnnnnn | nnnnnnnnnn | nnnnnnnnnn | nnnnnnnnnn | nnnnnnnnnn | nnnnnnnnnn | 8820 |
| nnnnnnnnnn | nnnnnnnnnn | nnnnnnnnnn | nnnnnnnnnn | nnnnnnnnnn | nnnnnnnnnn | 8880 |
| nnnnnnnnnn | nnnnnnnnnn | nnnnnnnnnn | nnnnnnnnnn | nnnnnnnnnn | nnnnnnnnnn | 8940 |
| nnnnnnnnnn | nnnnnnnnnn | nnnnnnnnnn | nnnnnnnnnn | nnnnnnnnnn | nnnnnnnnnn | 9000 |
| nnnnnnnnnn | nnnnnnnnnn | nnnnnnnnnn | nnnnnnnnnn | nnnnnnnnnn | nnnnnnnnnn | 9060 |
| nnnnnnnnnn | nnnnnnnnnn | nnnnnnnnnn | nnnnnnnnnn | nnnnnnnnnn | nnnnnnnnnn | 9120 |
| nnnnnnnnnn | nnnnnnnnnn | nnnnnnnnnn | nnnnnnnnnn | nnnnnnnnnn | nnnnnnnnnn | 9180 |
| nnnnnnnnnn | nnnnnnnnnn | nnnnnnnnnn | nnnnnnnnnn | nnnnnnnnnn | nnnnnnnnnn | 9240 |
| nnnnnnnnnn | nnnnnnnnnn | nnnnnnnnnn | nnnnnnnnnn | nnnnnnnnnn | nnnnnnnnnn | 9300 |
| nnnnnnnnnn | nnnnnnnnnn | nnnnnnnnnn | nnnnnnnnnn | nnnnnnnnnn | nnnnnnnnnn | 9360 |

```
nnnnnnnnnn nnnnnnnnnn nnnnnnnnnn nnnnnnnnnn nnnnnnnnnn nnnnnnnnnn      9420
nnnnnnnnnn nnnnnnnnnn nnnnnnnnnn nnnnnnnnnn nnnnnnnnnn nnnnnnnnnn      9480
nnnnnnnnnn nnnnnnnnnn nnnnnnnnnn nnnnnnnnnn nnnnnnnnnn nnnnnnnnnn      9540
nnnnnnnnnn nnnnnnnnnn nnnnnnnnnn nnnnnnnnnn nnnnnnnnnn nnnnnnnnnn      9600
nnnnnnnnnn nnnnnnnnnn nnnnnnnnnn nnnnnnnnnn nnnnnnnnnn nnnnnnnnnn      9660
nnnnnnnnnn nnnnnnnnnn nnnnnnnnnn nnnnnnnnnn nnnnnnnnnn nnnnnnnnnn      9720
nnnnnnnnnn nnnnnnnnnn nnnnnnnnnn nnnnnnnnnn nnnnnnnnnn nnnnnnnnnn      9780
nnnnnnnnnn nnnnnnnnnn nnnnnnnnnn nnnnnnnnnn nnnnnnnnnn nnnnnnnnnn      9840
nnnnnnnnnn nnnnnnnnnn nnnnnnnnnn nnnnnnnnnn nnnnnnnnnn nnnnnnnnnn      9900
nnnnnnnnnn nnnnnnnnnn nnnnnnnnnn nnnnnnnnnn nnnnnnnnnn nnnnnnnnnn      9960
nnnnnnnnnn nnnnnnnnnn nnnnnnnnnn nnnnnnnnnn nnnnnnnnnn nnnnnnnnnn     10020
nnnnnnnnnn nnnnnnnnnn nnnnnnnnnn nnnnnnnnnn nnnnnnnnnn nnnnnnnnnn     10080
nnnnnnnnnn nnnnnnnnnn nnnnnnnnnn nnnnnnnnnn nnnnnnnnnn nnnnnnnnnn     10140
nnnnnnnnnn nnnnnnnnnn nnnnnnnnnn nnnnnnnnnn nnnnnnnnnn nnnnnnnnnn     10200
nnnnnnnnnn nnnnnnnnnn nnnnnnnnnn nnnnnnnnnn nnnnnnnnnn nnnnnnnnnn     10260
nnnnnnnnnn nnnnnnnnnn nnnnnnnnnn nnnnnnnnnn nnnnnnnnnn nnnnnnnnnn     10320
nnnnnnnnnn nnnnnnnnnn nnnnnnnnnn nnnnnnnnnn nnnnnnnnnn nnnnnnnnnn     10380
nnnnnnnnnn nnnnnnnnnn nnnnnnnnnn nnnnnnnnnn nnnnnnnnnn nnnnnnnnnn     10440
nnnnnnnnnn nnnnnnnnnn nnnnnnnnnn nnnnnnnnnn nnnnnnnnnn nnnnnnnnnn     10500
nnnnnnnnnn nnnnnnnnnn nnnnnnnnnn nnnnnnnnnn nnnnnnnnnn nnnnnnnnnn     10560
nnnnnnnnnn nnnnnnnnnn nnnnnnnnnn nnnnnnnnnn nnnnnnnnnn nnnnnnnnnn     10620
nnnnnnnnnn nnnnnnnnnn nnnnnnnnnn nnnnnnnnnn nnnnnnnnnn nnnnnnnnnn     10680
nnnnnnnnnn nnnnnnnnnn nnnnnnnnnn nnnnnnnnnn nnnnnnnnnn nnnnnnnnnn     10740
nnnnnnnnnn nnnnnnnnnn nnnnnnnnnn nnnnnnnnnn nnnnnnnnnn nnnnnnnnnn     10800
nnnnnnnnnn nnnnnnnnnn nnnnnnnnnn nnnnnnnnnn nnnnnnnnnn nnnnnnnnnn     10860
nnnnnnnnnn nnnnnnnnnn nnnnnnnnnn nnnnnnnnnn nnnnnnnnnn nnnnnnnnnn     10920
nnnnnnnnnn nnnnnnnnnn nnnnnnnnnn nnnnnnnnnn nnnnnnnnnn nnnnnnnnnn     10980
nnnnnnnnnn nnnnnnnnnn nnnnnnnnnn nnnnnnnnnn nnnnnnnnnn nnnnnnnnnn     11040
nnnnnnnnnn nnnnnnnnnn nnnnnnnnnn nnnnnnnnnn nnnnnnnnnn nnnnnnnnnn     11100
nnnnnnnnnn nnnnnnnnnn nnnnnnnnnn nnnnnnnnnn nnnnnnnnnn nnnnnnnnnn     11160
nnnnnnnnnn nnnnnnnnnn nnnnnnnnnn nnnnnnnnnn nnnnnnnnnn nnnnnnnnnn     11220
nnnnnnnnnn nnnnnnnnnn nnnnnnnnnn nnnnnnnnnn nnnnnnnnnn nnnnnnnnnn     11280
nnnnnnnnnn nnnnnnnnnn nnnnnnnnnn nnnnnnnnnn nnnnnnnnnn nnnnnnnnnn     11340
nnnnnnnnnn nnnnnnnnnn nnnnnnnnnn nnnnnnnnnn nnnnnnnnnn nnnnnnnnnn     11400
nnnnnnnnnn nnnnnnnnnn nnnnnnnnnn nnnnnnnnnn nnnnnnnnnn nnnnnnnnnn     11460
nnnnnnnnnn nnnnnnnnnn nnnnnnnnnn nnnnnnnnnn nnnnnnnnnn nnnnnnnnnn     11520
nnnnnnnnnn nnnnnnnnnn nnnnnnnnnn nnnnnnnnnn nnnnnnnnnn nnnnnnnnnn     11580
nnnnnnnnnn nnnnnnnnnn nnnnnnnnnn nnnnnnnnnn nnnnnnnnnn nnnnnnnnnn     11640
nnnnnnnnnn nnnnnnnnnn nnnnnnnnnn nnnnnnnnnn nnnnnnnnnn nnnnnnnnnn     11700
```

| | |
|---|---|
| nnnnnnnnnn nnnnnnnnnn nnnnnnnnnn nnnnnnnnnn nnnnnnnnnn nnnnnnnnnn | 11760 |
| nnnnnnnnnn nnnnnnnnnn nnnnnnnnnn nnnnnnnnnn nnnnnnnnnn nnnnnnnnnn | 11820 |
| nnnnnnnnnn nnnnnnnnnn nnnnnnnnnn nnnnnnnnnn nnnnnnnnnn nnnnnnnnnn | 11880 |
| nnnnnnnnna ctttatcaaa aaattgatgg ggagagtttg ttgaagctca gagtgaggat | 11940 |
| ggatgtagaa catttcaagt gcttcatatc cagaaaatca gtagtcctcc atctgagttg | 12000 |
| tagacacagg aaaggagttg aagatgaatg gagtaggaat gtaaaagcct tatctttacc | 12060 |
| ctcctcagct ttaggtctta acaagaatga gcctccctta gtctttcttt atgcccctgt | 12120 |
| ccctgaatgt tggtgatgac attgttttc ctgtattgaa tacaaaaata tggccagtaa | 12180 |
| tttaggaatc aagaggatat aattcggaag tagactgttg tgtttaggag ttttcttc | 12240 |
| cattgtggaa ttgagtagca gcggtatata tgctatgtct ggtaaaatgg gccatacagt | 12300 |
| agtctaagac atgaggagac cttaaggagc ttggacttag ttgaggtgac cagactattt | 12360 |
| aatctgctta ggtgccacag caaaatacca tagagtaggt ggtttaaaca gcagacattt | 12420 |
| atgatctcat aggtttgcag tctggaagtc agggtgccag cgtggttggt tcccgatcag | 12480 |
| ggctctcctc ctggattgcc cgtgtcctca catggcatag agagtatg acagcatgag | 12540 |
| caagctctcg ttttatcttc ttataagagc actgatccca tcatgagggc cccattctca | 12600 |
| tgacctcatc taaacctgat tattttccaa aggccccatc tccaaatgcc atcacattga | 12660 |
| gagttaaggc ttcaacatat gaatttggtg gggaaaccca gacatttcaa tccataattc | 12720 |
| aggcagatat ttgggaagta acacagttga agcactgaat gctatatttc gtactatcta | 12780 |
| aagaatctag gatgtaataa atttaagatg cttcattgcc aattaaatta agatacaatg | 12840 |
| ctttttttgat tacttagaat tttttaaaga gctcttttag agttagacat agattttgt | 12900 |
| catatgtcac ttgcacattc aataagatgg aaaacacaag tgaaaaaaca cataaggaat | 12960 |
| tgctaaattt cacatatta gagtctgcct tctgaattgt ttttggagtc agagttgtta | 13020 |
| atacctgtaa ttttccgtta aacatcctct gtgccgccaa gagaattggt gatgtagcat | 13080 |
| tcctttcaag atcccaaaaa agaatgcgaa ggttttggtg ctggccttca gctttgcaat | 13140 |
| tatgcaaagc cagcctactt tgactgctgc ttagggattc cccatcttct acttccttcc | 13200 |
| cagtccattt ggttcctaga gggtgaaatg aatgctccag tatcatttct ggaatttct | 13260 |
| ttcaggctgt tgactgtcat atgcaaatgt catgctggca gttttgttat tttcccatgt | 13320 |
| gtaagcaatg acaacatcat aattggcttc tgtctgatag caattgtaag aggaatccca | 13380 |
| atttctgaaa tgttacccaa aaaagtgact ttaattgacg aagtatgatg atgtagaagg | 13440 |
| ataggcaaga aatgcaaaag gtaatttaga aaggtttcat gggtaaaatg tgacctatgt | 13500 |
| gatctagggc tataaaggat ttcaataagc agaagcacga ggtgggttgt tgaagaaagc | 13560 |
| actaaatgtt tttggataaa gaatataata atttgagagt aaagggtaga gggagggtta | 13620 |
| tgtaggtaag tagttgtaag atggggaaag attgggtagt atttagcatt tatccttaat | 13680 |
| gttgacttca gtgtagttct ctttgtgtgt tttctagtat aaactgcata catgaaagtt | 13740 |
| aagaatcttg tgttaagtcc catataggaa ggaagtagat aggaaaacca aactggaaaa | 13800 |
| atgtatggag atgttggtga aatgacagga acgaaagcag cttgtctgag cttgatctct | 13860 |
| tcacttcctc agtggtggtt ctgagcgctg gtttggctga actccactta ccagggaaaa | 13920 |
| gggcataaag taaacagggt ttgtgtggaa gaagtggagt agaacaaagt ggagaggatc | 13980 |
| tctgttcatt tagtgtatct gacagtgtgc ttgtcaagtc ataaaacact tgaggatgga | 14040 |
| aatctggaag tcattgtata catttcttc tttccctaac atctagtcag ttacagtttc | 14100 |

-continued

```
tgccagttct tttgcttttt ccatgttttt ggaggctgtt cctcttcgct ccacatgtag    14160
taaatgctct agttcatgac ccatgtctta tctggactgc catgtcagct tcctaactca    14220
tccattcaca gcaccagtga ctgtaaaaca gcattagtga ggataaaaca gtggctgtca    14280 aactttttg actgtggccc ccagtaaaaa tacactttgt attgcaactt atgtatactt    14340
tatatatgta tgaataatta aaacaaaagg ttgattcaag aaaaatcttt acatttaccc    14400
tgtgccatgc aatcttatat cttgtattct tttctgtttc attttttaa atgtgtgctt    14460 gccatccact aaattgattc cggagttgga aaaacactga cctgacaact aatatcacca    14520
tgttattcct taaactctcc gatggcttct tactatcttc atgataaatt tgaagccctc    14580
aacatcagca taccagaacc ttcatgacct aacccttacc tagttattct aatctattat    14640
ttacctgatc cactcagctc acatttcatt ccaatagaca agtaaagttt tttgtaattc    14700
cttgtagctt gcctttcttc atggtgtcca ctctgttgaa aatctactac cctccatttc    14760
ttcagtgctt tactgcttac tcctacccat tcctggggct caagtcaggc ccctataacc    14820
aggatgcttt tcctaacact ccttgcccta ccaccaggct gggttaggta gttctccatt    14880
atataatgtg gttctcaatg ttgttacctg tttattatta tgtgtttttc tcttattgtc    14940
ccataaaata gtgaatattc gagaggataa ggaagtctcc cattaagcat ccctaatgtt    15000
tagtatgtaa catgttggca ttggttggat gaatgagaaa aaaaaagat tcttctgttt    15060 ggaaggaaga tacaactggt atcccttaag tcttttcttt tttttttttt ttttcctttc    15120
tctatagaca aggtctcacc atcacccagg ctggagtgca gtggtgcaat cacagctcac    15180 tacaccctg tactcctggg ctcaagtgat cctgctacct cagcctccct agtagctggg    15240
actgcaggca tgcaccacca tgctcagctc attttaaaaa aatttttttt gttgagacag    15300
agtcttgcta tgttgcctag gctggtcttg aactcctggg ctcaagtgat cctcctgcct    15360
cagcctccca gagtgctagg attataggca tgatccactg cacctggccc cttaagacct    15420
ttaattgcag agcagcagag gacaaatgac ataaatacag gatttgactt tcattttaa    15480 gtatcaaatt agtgatgggt tgacaaacaa gtcatacaga atgttcatga atcagttcgg    15540
cccaggtaac tcataaccca agacctttgg gtcaatgaaa ttctgccacc taagtagcac    15600
catccaatga tgtcatacct aaaaaggaaa ttgagttgta gaattttagg ttttaggatt    15660 cttctctaa aactgaggag ctgtgccact cttcaaagcc tcacaattac atttcattgg    15720
ttcttatgcc atctgggttc tggttagagg gctgatggaa gtactcaaga aatattggaa    15780
gtactcaaga aatattagaa ggtgggaaga aggtacctct cttgttcttg tcagtggcag    15840
caccaacagt gggactttgg gtctctgggt tccagctcag cagcagaggt actagtactg    15900
tagctccagc agcttcagca ggagtgcagg ctcatgggat cagagaacca ccttttccgc    15960
tttgttcttc cagcccagcc aacaagtttg tagctatttc cctgcattaa aactcccctc    16020
tgtttgaaat atctatagta attttctttt tcctgactaa tacaacctgt taaagaagct    16080
gaagctctgg taagttaaat gcccaacaat ggtcttgagt agctagtgat ttttgttgct    16140
attggtaagt aaatctagac actactttt agtcccctttt ttaaaagagg actggtttat    16200
ctatgatgaa tacatgattg attgattgat tgattgattg attttactt tttcttttt    16260 tttttttgag acggagtctt gctctgtcac ccaggctgga gtgcagtaac atgatctctg    16320
ctcactgcaa gctcctcctc ccgggttcac gccattctcc tgcctcagcc tcctgagtag    16380
ctggggctac aggcatctgc caccacgccc ggctaatttt ttgtatttt ttgtagagac    16440
```

| | |
|---|---|
| ggggttttcac catgttagcc aggatggtct cgatctcctg accttgtgat ccgcctgcct | 16500 |
| cagcctccca aagtgctgag attacaggca tgagccacca cgcccggcct aatttattaa | 16560 |
| aactttcggg tggtcaggta attctgattt gtcagccata tttctaaatt atcaatnnnn | 16620 |
| nnnnnnnnnn nnnnnnnnnn nnnnnnnnnn nnnnnnnnnn nnnnnnnnnn nnnnnnnnnn | 16680 |
| nnnnnnnnnn nnnnnnnnnn nnnnnnnnnn nnnnnnnnnn nnnnnnnnnn nnnnnnnnnn | 16740 |
| nnnnnnnnnn nnnnnnnnnn nnnnnnnnnn nnnnnnnnnn nnnnnnnnnn nnnnnnnnnn | 16800 |
| nnnnnnnnnn nnnnnnnnnn nnnnnnnnnn nnnnnnnnnn nnnnnnnnnn nnnnnnnnnn | 16860 |
| nnnnnnnnnn nnnnnnnnnn nnnnnnnnnn nnnnnnnnnn nnnnnnnnnn nnnnnnnnnn | 16920 |
| nnnnnnnnnn nnnnnnnnnn nnnnnnnnnn nnnnnnnnnn nnnnnnnnnn nnnnnnnnnn | 16980 |
| nnnnnnnnnn nnnnnnnnnn nnnnnnnnnn nnnnnnnnnn nnnnnnnnnn nnnnnnnnnn | 17040 |
| nnnnnnnnnn nnnnnnnnnn nnnnnnnnnn nnnnnnnnnn nnnnnnnnnn nnnnnnnnnn | 17100 |
| nnnnnnnnnn nnnnnnnnnn nnnnnnnnnn nnnnnnnnnn nnnnnnnnnn nnnnnnnnnn | 17160 |
| nnnnnnnnnn nnnnnnnnnn nnnnnnnnnn nnnnnnnnnn nnnnnnnnnn nnnnnnnnnn | 17220 |
| nnnnnnnnnn nnnnnnnnnn nnnnnnnnnn nnnnnnnnnn nnnnnnnnnn nnnnnnnnnn | 17280 |
| nnnnnnnnnn nnnnnnnnnn nnnnnnnnnn nnnnnnnnnn nnnnnnnnnn nnnnnnnnnn | 17340 |
| nnnnnnnnnn nnnnnnnnnn nnnnnnnnnn nnnnnnnnnn nnnnnnnnnn nnnnnnnnnn | 17400 |
| nnnnnnnnnn nnnnnnnnnn nnnnnnnnnn nnnnnnnnnn nnnnnnnnnn nnnnnnnnnn | 17460 |
| nnnnnnnnnn nnnnnnnnnn nnnnnnnnnn nnnnnnnnnn nnnnnnnnnn nnnnnnnnnn | 17520 |
| nnnnnnnnnn nnnnnnnnnn nnnnnnnnnn nnnnnnnnnn nnnnnnnnnn nnnnnnnnnn | 17580 |
| nnnnnnnnnn nnnnnnnnnn nnnnnnnnnn nnnnnnnnnn nnnnnnnnnn nnnnnnnnnn | 17640 |
| nnnnnnnnnn nnnnnnnnnn nnnnnnnnnn nnnnnnnnnn nnnnnnnnnn nnnnnnnnnn | 17700 |
| nnnnnnnnnn nnnnnnnnnn nnnnnnnnnn nnnnnnnnnn nnnnnnnnnn nnnnnnnnnn | 17760 |
| nnnnnnnnnn nnnnnnnnnn nnnnnnnnnn nnnnnnnnnn nnnnnnnnnn nnnnnnnnnn | 17820 |
| nnnnnnnnnn nnnnnnnnnn nnnnnnnnnn nnnnnnnnnn nnnnnnnnnn nnnnnnnnnn | 17880 |
| nnnnnnnnnn nnnnnnnnnn nnnnnnnnnn nnnnnnnnnn nnnnnnnnnn nnnnnnnnnn | 17940 |
| nnnnnnnnnn nnnnnnnnnn nnnnnnnnnn nnnnnnnnnn nnnnnnnnnn nnnnnnnnnn | 18000 |
| nnnnnnnnnn nnnnnnnnnn nnnnnnnnnn nnnnnnnnnn nnnnnnnnnn nnnnnnnnnn | 18060 |
| nnnnnnnnnn nnnnnnnnnn nnnnnnnnnn nnnnnnnnnn nnnnnnnnnn nnnacaggca | 18120 |
| cacaccacca tgcctggcta attttttgta tttttagtaa cagggtttca ccatgttagc | 18180 |
| caggctggca tcgaattcct gacctcaggt gatccgcccc cctcaacctc ccaaagtgct | 18240 |
| gggattacag gcgtaagcca ccatgcctgg cctgtattta atcttcatag cagttttatg | 18300 |
| aggtaggtgg tgtcatcccc actttacaga gaagtgggtt aatgtagggt tcaaatgata | 18360 |
| aatagtaact tgctgatagt cactggcaat tttaatttgt cttcagtgta gtagagtaac | 18420 |
| tgtgaactgt tagagttatg aaactgacat ggaaagttgt ataccaaagg agtcttagga | 18480 |
| ctgtccatgg atactgttat gtatcatttc acttatattg gcttcagctt gcgatttctc | 18540 |
| tactgtaagt ggtgagaatt gatcagatag ttaaggaagg tccttagata atgcagtata | 18600 |
| cttattaaca tacagacatc aagaagcaga aatatataga catcttcctt tttggttcta | 18660 |
| ataggcttc gtgggacaca tatgcaacat gcctatgatt tttacaagcc tgatatgcta | 18720 |
| tctgaatatc ctatagtaga tggaaaactc tccatacagt gctacctcag tgcattagac | 18780 |
| cgctgctatt ctgtctactg caaaaagatc catgcccagt ggcagaaagg taagttttac | 18840 |

```
ccattttcct tggttttggt atgagttgag agcagtctaa tgtactaggt atctttggta    18900
ggcaactact ttgtgggcat tcttcattta atatccttt  accattaatt cctcattcac    18960
caaacaacat tttcccatag tttctgggaa agtgtaattt actagaagag gtaaactttg    19020
gaactgaggt gtatctctgc aaaaatattt aggtcggttt accccttgta agaaaatcaa    19080
agtggagaaa agaaggtaag ttgaattttg ttcatctttt gagagaggta ttttaacaag    19140
gttttggact acagctgtga ttcagggaaa gctaatgaaa atgaattact aaagtgatct    19200
taccccaaaa ataatctttt tgcacttgac ctgtgaattt gtatttgttt tttactgtt    19260 atcattaatc tggaaatttg ttgaggcact gaaaggacag tatttgagtt aatgctatca    19320
taacacatta ttcataaag  tatacttttt ctgtagtcca actttgcttt ttagaggtta    19380
tgagaagggg ttaaaaatca tattcaatga caaatatcag tgaatttagt cgctctggat    19440
aagaagcatt cttgcagtat atattaacag aatagtggtt ttctaacttt tttattagga    19500
cccacagtaa gaagtacatg ttacattgta tgtgtatgcc agactgaaac aaaaatgtca    19560
tgacattact tacccttgct gcaagttatt cagtttgcta ttttttctact gcattttgtt    19620 ttttaaaata ctctttttatt taaaaaaaat actaatcctg acccactaaa ttgattatgt    19680
aacctgctaa tgtgtatgaa tcttaaattt gaaaattagt gacatagtac atattgtttc    19740
atctttgagt gtcttttttaa atgtatactt taaggtatag agaggtttca ttatacagtg    19800
tatttgtggt tgctgtttaa acatatacaa atatcctagc tttattctaa agtcaaactt    19860
taaaatttca tggcttatat gaatttcata gtttccttgg acttctcttt cagagggaaa    19920
tgataaagat tttaccttga atgattttgg cttcatgatc tttcactcac catattgtaa    19980
actggttcag aaatctctag ctcggatgtt gctgaatgac ttccttaatg accagaatag    20040
agataaaaat agtatctata gtggcctgga agcctttggg taagaggagc tattatgagt    20100
tttttccttc tatattagag catttttaat atctgttaag ctgttatttg tacagacctg    20160
agaaattgag agtcagaaga atcttagaag tcatccagtc taatctgtgt gtctcagtca    20220
gtgaagaatc taagtccaga gaggtggtag ttaacatgca caaattcttt agacatttct    20280
attcagattt tctgatttat ttctttcagc tccattcatg ttgtcacgat aaagtaactg    20340
cacaagggcc tatattcact acagcagcct cttaactcct tacctctctc agcacccctg    20400
cccccatgcc cttttccatc ctgcacactg ccacagctaa agtcagcttt tgtactccac    20460
ctgtcttttt ctcactttag gctccctagc atgctatgtg tgttcaactc gttctgtttc    20520
tccctgtgtc tcttgtgtgt cctttctcta tctgataaaa ttatacttga cttttaaaac    20580
ttggctcctg taataccatg acttttctaa ctaaataaac attattatgg acttgaaata    20640
gtattctatt cagttgatga atattcagtt gattgaatat tctattcatt gaagccaata    20700
taagtgaata taaatataaa gctacagtgc gtcttttaac ctattcaaat caagcaggct    20760
taacttgatt atgaaaactt ttgagaaaaa gaaccatata tatacaactg ttatgatttc    20820
tatagcaatt agattgctgc tacttggctt ttaataaatg agaaaacaat tatatacact    20880
taaagatttg aatcctaatt aggcctgctg tttagtgtaa taaaaacata ggctttaaac    20940
actgtaaaac tgtaaaataa atcttttcagg gatgttaaat tagaagacac ctactttgat    21000
agagatgtgg agaaggcatt tatgaaggct agctctgaac tcttcagtca gaaaacaaag    21060
gcatctttac ttgtatcaaa tcaaaatgga aatatgtaca catcttcagt atatggttcc    21120
cttgcatctg ttctagcaca gtaagtataa atttcaccta ctactaact  ccccttattt    21180
```

```
gggagatgtt agatttctaa gaccaaatct agtgtcaagc atgttggtgg tagatcacag   21240
aaaattttat cttgaggctc tctaatctgc tattgtccat tgacttgaaa gatgtatggg   21300
ttgaggctac agttcttcca gaagtatttg ttaatttcat actggctttc ctggcttctg   21360 tttcatggt tttttaattc ttgacctaca gttgaaccat aaatacctgg ttgatgaagt   21420
aacttgtttt gtggcatgac tttcacaagc tctgtcattc cccacaagat gaaaactcac   21480
atgctgcaat attaaaacta agttatattc cctactgcaa tattaacact ttgagttaga   21540
tccttaaaac tttaagttag attctacttt tacttatagc ctaaattttt attgctactt   21600
ttatagcttc ccacacgctg tagctttgga tcagttaaac ttctgaacta ttgttacacc   21660
ctacataggt actcacctca gcaattagca gggaagagaa ttggagtgtt ttcttatggt   21720
tctggtttgg ctgccactct gtactctctt aaagtcacac aagatgctac accgggtaag   21780
tgctgaatct ttcaacaaga atgtattgag aactgagtcc aggcacagtg gctcacaccc   21840
gtaatcccag cagtttggga ggccgaggcg ggcagatcac ctgaggtcag gagttcgaga   21900
ccagtctggc taacatggct gaaaccccat ctctactaaa aatacaaaaa ttagccaggt   21960
gaggtggtgc atgcctgtag tcctagctac ttgggaggct gaagtaggag aatcacttga   22020
atccaggaga gggaggttgt ggtgagccaa gatcacacca ctgtgctcca gcctgggtga   22080
cagagcgaga ctctgtcaaa aaaaaaaaaa aaaatgtat tgagaactac tctggggaag   22140
ttgatttagc agtcttctca agtgagcacc tgaatctgtc ccacagatca ttacaatatt   22200
ttagtcttca ttacttcttt cagtaggttt ttactctctg ccctaaaaat ctatccaaaa   22260 aaaaaaaaa attctacctt atctggataa aggataggac taagttatct aatttttata   22320
ggcttatggt cttggctata tttaaggtca cttttgtgct ttccctgagc aggaaagagc   22380
aaaaatgtag agataaactg atgaaaactt gacattactt tttaaaatta taccatgggc   22440
caggtgcaat ggctcacacc tataatccca acacttcagg aggctgaggt gggaggattg   22500
cttgaggcca gatgttcaag gccaacctga gcaacatagt gagacccat ctctataaaa   22560 aataataaaa ataaaataat tataccatgg attaattgta gacaagttat ttatagtttc   22620
aaattatgcc tgtttcctaa cttgtctagt ggcagatact caataataga tttctagtct   22680
gacatcatag gagatttgtc aaataggtat catcttatct tttaactaat cagtagccag   22740
tagttttaat gaaaatgaaa agttgttttg cctcatttgg caacattta cttaggcttc   22800 ttttggacat gatttttcaa aaaaatcttt taatgttgaa ttattcacta ttttagggtc   22860
tgctcttgat aaaataacag caagtttatg tgatcttaaa tcaaggcttg attcaagaac   22920
tggtgtggca ccagatgtct tcgctgaaaa catgaagctc agagaggaca cccatcattt   22980
gggtaaaaat attaaatgtt ctttaagtta acccatttgg agggctgata tcattaagga   23040
tgctacatat acgataagga tatcaagact ttactcagta ctaatctgat gtcagtgaaa   23100
attattggga tatatgaaac ttatctttag ctttattacc agatgaattg tatatcaaa   23160 ctaattgtag atattctctc cctttccttt agtcaactat attccccagg gttcaataga   23220
ttcactcttt gaaggaacgt ggtacttagt tagggtggat gaaaagcaca gaagaactta   23280
cgctcggcgt cccactccaa atgatgacac tttggatgaa ggagtaggac ttgtgcattc   23340
aaacatagca actgaggtaa ataaaagagt tcccatctcc atatcttagg gtttaggaga   23400
cctaactggg atttagcaac ataaataaat gtcagtaaag aagagtaagg gctctgggag   23460
tagattctag ctgtactatt tccaattgta taaagtgctt tgcatttgaa ttattaatat   23520
tttaagaata tacagtaaag gccgggtgcg gtggctcacg cctgtaatcc cagcactttg   23580
```

-continued

```
ggagactgag gcaggcagat cacgaggtca ggagatcaag accatcctgt ccaacatggt    23640
gaaaccctgt ctctactaaa aatacaaaaa ttagttgggc ttggtggcac gtgcctgtaa    23700
ttccagctac tcaggaggct gagtcaggag aatggcttga accagggagt cagaggttgc    23760
agtaagctga gatcacacca ctgcactcca gcctggcgac agagcaagat tccatctcaa    23820
aaaaaaaaaa aaaaaaaaaa aagaatatac agtaaatact aggttttatt aatgatacca    23880
ggatttaaag gaagactgat atagagagaa ggttcatttg tggtgtgtgt ctttgtgaga    23940
gatggagtag agggacaagg atcctttcac atctcatccc agatcatggt caaaatctgt    24000
cctcaaattg tcaagaagta acaatcatag ctatgatttg aattcctgtt acctgctagg    24060
cactttactt acgttttctt atttaatcct tacaacaacc tccttgaagt ttataaatga    24120
tactgtcctc cctttagaga tgagcctcca agaagttaca ttacttgccc aggattatag    24180
gtagtaagta ttaaagccag gttataaact aaggacttta taaccttgaa actacttatt    24240
tatctgctta ctacaagttt ggtaaatgga tagtcttgct ttttgctatt atacaaatta    24300
ggtagcaagt caaaccgcca ctgtttgagt tgcaaataca agacgtaaca agtaaaatac    24360
tgttacgtgg tgggtctctg tggcaggctt cctctccccc ccatatggat aattgtatac    24420
taaattcacc ataaggtgaa aaatggatat tgagttccct tcatgaaaag ttatataaaa    24480
tatatattta gcataaactt ctccagagtt gtcctttatt aagtttcttt acagaaactt    24540
taattggtgc catgattctt gtgggggaaa gaatcataag agccatcaac ttttttcctt    24600
tcattttagc atattccaag ccctgccaag aaagtaccaa gactccctgc cacagcagca    24660
gaacctgaag cagctgtcat tagtaatggg gaacattaag atactctgtg aggtgcaaga    24720
cttcaggggtg gggtgggcat ggggtggggg tatgggaaca gttggaggaa tgggatatct    24780
ggggataatt ttaaaggatt acatgttatg taaattttta tgtgactgac atggagcctg    24840
gatgactatc gtgtacttgg gaaagtctct ttgctctatt tgctgacatg cttcctgttg    24900
tggtctggcc aatgccaaat gtactcgaat gatgttaagg gctctgtaaa acttcatacc    24960
tctttggcca tttgtatgca tgatgtttgg ttttttaaaca tggtataatg aattgtgtac    25020
ttctgtcaga agaaagcaga ggtactaatc tccaattaaa aaatttttta acatgtaaga    25080
attttgtact ttgaacaaca agattacaga aagtacctgt ggttttttgga aaacatttct    25140
agcttgggga atgtgacaac attccccagt gtggtaaaat tggggtaaaa tgtggtaaaa    25200
tgtgatacgc acaaaccctt tgaaaatagc aaaacaaaca tgcccttttt ctaaaattga    25260
taaatcctaa agaggaagaa aagagctggg acaataaaac actggctctg gaatctggaa    25320
tgttaagtcc aggccagcag tgacaaaagt tattgtaatg acctctgaac agagaaacac    25380
tgccattgaa gaggcttctg gtatagaaaa catggtacat tcaggagctg tgaatatagc    25440
tctaggtgtg ctcctgaatc agttcatggt agattatgct gaacaacagt gagatgttat    25500
tggaggtgtg gatgagggag tttgttgttg cagtccttct ttgcacctta ttttaaagaa    25560
taaatgaaac attttctgg ttactttttt aaaaatttaa aatggaaggg aagaatagg g    25620
gcagggcatt attaggctat ttctgatgct tcagtgttat aaattcaaca tagaggctga    25680
caacctaaat tcatggtgta acacagctct tttccttttc cttttttttt tttttttggt    25740
atctgttcaa tgaaaataag gtatgaccca agttttttacc tagtctgact agaagtattc    25800
cacttcaagg tctgaagtag gactttttacc ttaaaaaaca acaacaaaca aaactatcac    25860
acaggataga taagaagatt ggttaaacag ttttgtgtag atcttttttgg tgctgaacta    25920
```

-continued

```
tgacatgagc cttatagatt gtaaaatagg gatagttgga actaatgtac agaactaaat      25980
tttttaaact ttatttgctg ttaaattctg tgaagtttca gttatctaaa ataaatatac      26040
acaaatatga aatataatgt ttcagattgc aaggtaatat gtaatagtag tgtttgtaag      26100
atactcttgt ctaatattaa ctagtagtat tttgatttgt acagtcataa tttgttaaaa      26160
tgacttcatt taacattcac tgatgtagat taataatgta agttctgatt taaagaatgg      26220
tggcaaaatg gtgcatgtaa tacttttgca agtgttgggg agatcggtat gttttgaaaa      26280
gagtaattta acttttgggt gccaggaaat gggttttctc aaagtccatt gccggcaatg      26340
ggcaggcctg caaatactgg cacagagcat taatcataca ccttattaac ggtgaggtga      26400
ataactttga aataaagttt tagagaaatg tttcagatac ttgagtattc tttttcactc      26460
ttgaactaac aacttcggca agaaatcagc taatattcta tttttaaata tgggcattaa      26520
tttcatttca gttcgttcac tcattccatt catttatcat ttcacaaaca tttgaaatcc      26580
taatataagc aaggtgctct gtttaaggca gaaatttgaa aatgtacaag atatatggtc      26640
ttgtctttaa ggagctgttc atctagaatg gaggaattta cactgataat tattcctaca      26700
cttgaaacaa agaaattaac tctcaaattg cgtggcaagc atatatagac tttgctataa      26760
atatttatga aatgagttac tgttttcctt aaaaaagcta agactaaggg ctggcaatca      26820
aataagagca aatttagtgg tgaacgtaga actgcccact accagctaga gtctccaacc      26880
taaaagtccc atgttgctag tgatccccag gggttttata gaaggaatcc ctgcattggc      26940
agtaattttg gattagatga tccctaagag caccatcaag tcttaggatt ctatgaatta      27000
ggaaataaac caaattatat attttctaat actgatcagc tcatatttta tcatcatgtc      27060
atgtctggct ttcatactgg gaatacagat atagaaggaa tcgacacaac taatgcatgc      27120
tatggaggca cagctgctgt cttcaatgct gttaactgga ttgagtccag ctcttgggat      27180
ggtatgttac atgcctattc cccgccgtcc cccaaaattt ttttctaagg ttcaatagac      27240
ccaaatgaca ctttaattaa tgcaatacgc aaactttgt aatttatcct tgtttggata       27300
tattaagaaa gatattttac ctgtctgtca ttatccgaat tgtgaattgg ttatcttatc      27360
ttgtaggaca aatggtctat tcaaaattta gtcagatgga tgacagagcc ttggcagatg      27420
aattttaaaa aaaattaga gcattttctt tctttatcaa agaagggaaa agcatattct      27480
ggggaaaata taacagactt cagtttccat gtttggttat agtgttgaat tccttcttgt      27540
gaaataacaa aaaatatttt tcaggacggt atgccctggt agttgcagga gatattgctg      27600
tatatgccac aggaaatgct agacctacag gtggagttgg agcagtagct ctgctaattg      27660
ggccaaatgc tcctttaatt tttgaacgag gtaagtgctt gggaaagcat ttttgttttt      27720
tttagcacaa tatgctgaga aatttgaaaa tagaagtagg agctgtcgct tacttaatgg      27780
tcattaaatg caggtactac ttgctaagag ctttatgtgt gttatcatat ttatgttttt      27840
ttttctttt tttttttttt gagaccgagt ttcactcttg ttgcccaagc tggagtgcaa        27900
tggcacgatc tcggctcact gcaacctctg cccccaggtt caagtgattc tcctgcctca      27960
gcctcctgag tagctgggat tacaggcaca caccaccatg c                          28001
```

<210> SEQ ID NO 4
<211> LENGTH: 520
<212> TYPE: PRT
<213> ORGANISM: Human

<400> SEQUENCE: 4

Met Pro Gly Ser Leu Pro Leu Asn Ala Glu Ala Cys Trp Pro Lys Asp

-continued

```
  1               5                   10                  15
Val Gly Ile Val Ala Leu Glu Ile Tyr Phe Pro Ser Gln Tyr Val Asp
             20                  25                  30

Gln Ala Glu Leu Glu Lys Tyr Asp Gly Val Asp Ala Gly Lys Tyr Thr
             35                  40                  45

Ile Gly Leu Gly Gln Ala Lys Met Gly Phe Cys Thr Asp Arg Glu Asp
 50                  55                  60

Ile Asn Ser Leu Cys Met Thr Val Val Gln Asn Leu Met Glu Arg Asn
 65                  70                  75                  80

Asn Leu Ser Tyr Asp Cys Ile Gly Arg Leu Glu Val Gly Thr Glu Thr
                 85                  90                  95

Ile Ile Asp Lys Ser Lys Ser Val Lys Thr Asn Leu Met Gln Leu Phe
            100                 105                 110

Glu Glu Ser Gly Asn Thr Asp Ile Glu Gly Ile Asp Thr Thr Asn Ala
            115                 120                 125

Cys Tyr Gly Gly Thr Ala Ala Val Phe Asn Ala Val Asn Trp Ile Glu
            130                 135                 140

Ser Ser Ser Trp Asp Gly Arg Tyr Ala Leu Val Val Ala Gly Asp Ile
145                 150                 155                 160

Ala Val Tyr Ala Thr Gly Asn Ala Arg Pro Thr Gly Gly Val Gly Ala
                165                 170                 175

Val Ala Leu Leu Ile Gly Pro Asn Ala Pro Leu Ile Phe Glu Arg Gly
                180                 185                 190

Leu Arg Gly Thr His Met Gln His Ala Tyr Asp Phe Tyr Lys Pro Asp
            195                 200                 205

Met Leu Ser Glu Tyr Pro Ile Val Asp Gly Lys Leu Ser Ile Gln Cys
            210                 215                 220

Tyr Leu Ser Ala Leu Asp Arg Cys Tyr Ser Val Tyr Cys Lys Lys Ile
225                 230                 235                 240

His Ala Gln Trp Gln Lys Glu Gly Asn Asp Lys Asp Phe Thr Leu Asn
                245                 250                 255

Asp Phe Gly Phe Met Ile Phe His Ser Pro Tyr Cys Lys Leu Val Gln
            260                 265                 270

Lys Ser Leu Ala Arg Met Leu Leu Asn Asp Phe Leu Asn Asp Gln Asn
            275                 280                 285

Arg Asp Lys Asn Ser Ile Tyr Ser Gly Leu Glu Ala Phe Gly Asp Val
            290                 295                 300

Lys Leu Glu Asp Thr Tyr Phe Asp Arg Asp Val Glu Lys Ala Phe Met
305                 310                 315                 320

Lys Ala Ser Ser Glu Leu Phe Ser Gln Lys Thr Lys Ala Ser Leu Leu
                325                 330                 335

Val Ser Asn Gln Asn Gly Asn Met Tyr Thr Ser Ser Val Tyr Gly Ser
                340                 345                 350

Leu Ala Ser Val Leu Ala Gln Tyr Ser Pro Gln Gln Leu Ala Gly Lys
            355                 360                 365

Arg Ile Gly Val Phe Ser Tyr Gly Ser Gly Leu Ala Ala Thr Leu Tyr
            370                 375                 380

Ser Leu Lys Val Thr Gln Asp Ala Thr Pro Gly Ser Ala Leu Asp Lys
385                 390                 395                 400

Ile Thr Ala Ser Leu Cys Asp Leu Lys Ser Arg Leu Asp Ser Arg Thr
                405                 410                 415

Gly Val Ala Pro Asp Val Phe Ala Glu Asn Met Lys Leu Arg Glu Asp
            420                 425                 430
```

-continued

Thr His His Leu Val Asn Tyr Ile Pro Gln Gly Ser Ile Asp Ser Leu
         435                 440                 445

Phe Glu Gly Thr Trp Tyr Leu Val Arg Val Asp Glu Lys His Arg Arg
         450                 455                 460

Thr Tyr Ala Arg Arg Pro Thr Pro Asn Asp Asp Thr Leu Asp Glu Gly
465                 470                 475                 480

Val Gly Leu Val His Ser Asn Ile Ala Thr Glu His Ile Pro Ser Pro
                485                 490                 495

Ala Lys Lys Val Pro Arg Leu Pro Ala Thr Ala Glu Pro Glu Ala
             500                 505                 510

Ala Val Ile Ser Asn Gly Glu His
             515                 520

<210> SEQ ID NO 5
<211> LENGTH: 518
<212> TYPE: PRT
<213> ORGANISM: Human

<400> SEQUENCE: 5

Met Pro Gly Ser Leu Pro Leu Asn Ala Glu Ala Cys Trp Pro Lys Asp
1               5                   10                  15

Val Gly Ile Val Ala Leu Glu Ile Tyr Phe Pro Ser Gln Tyr Val Asp
            20                  25                  30

Gln Ala Glu Leu Glu Lys Tyr Asp Gly Val Asp Ala Gly Lys Tyr Thr
        35                  40                  45

Ile Gly Leu Gly Gln Ala Lys Met Gly Phe Cys Thr Asp Arg Glu Asp
    50                  55                  60

Ile Asn Ser Leu Cys Met Thr Val Val Gln Asn Leu Met Glu Arg Asn
65                  70                  75                  80

Asn Leu Ser Tyr Asp Cys Ile Gly Arg Leu Glu Val Gly Thr Glu Thr
                85                  90                  95

Ile Ile Asp Lys Ser Lys Ser Val Lys Thr Asn Leu Met Gln Leu Phe
            100                 105                 110

Glu Glu Ser Gly Asn Thr Asp Ile Glu Gly Ile Asp Thr Thr Asn Ala
        115                 120                 125

Cys Tyr Gly Gly Thr Ala Ala Val Phe Asn Ala Val Asn Trp Ile Glu
    130                 135                 140

Ser Ser Ser Trp Asp Gly Arg Tyr Ala Leu Val Val Ala Gly Asp Ile
145                 150                 155                 160

Ala Val Tyr Ala Thr Gly Asn Ala Arg Pro Thr Gly Val Gly Ala
                165                 170                 175

Val Ala Leu Leu Ile Gly Pro Asn Ala Pro Leu Ile Phe Glu Arg Gly
            180                 185                 190

Leu Arg Gly Thr His Met Gln His Ala Tyr Asp Phe Tyr Lys Pro Asp
        195                 200                 205

Met Leu Ser Glu Tyr Pro Ile Val Asp Gly Lys Leu Ser Ile Gln Cys
    210                 215                 220

Tyr Leu Ser Ala Leu Asp Arg Cys Tyr Ser Val Tyr Cys Lys Lys Ile
225                 230                 235                 240

His Ala Gln Trp Gln Lys Glu Ala Asn Asp Asn Asp Phe Thr Leu Asn
                245                 250                 255

Asp Phe Gly Phe Met Ile Phe His Ser Pro Tyr Cys Lys Leu Val Gln
            260                 265                 270

Lys Ser Leu Ala Arg Met Leu Leu Asn Asp Phe Leu Asn Asp Gln Asn

-continued

```
                     275                 280                 285
Arg Asp Lys Asn Ser Ile Tyr Ser Gly Leu Lys Ala Phe Gly Asp Val
    290                 295                 300

Lys Leu Glu Asp Thr Tyr Phe Asp Arg Asp Val Glu Lys Ala Phe Met
305                 310                 315                 320

Lys Ala Ser Ser Glu Leu Phe Ser Gln Lys Thr Lys Ala Ser Leu Leu
                325                 330                 335

Val Ser Asn Gln Asn Gly Asn Met Tyr Thr Ser Ser Val Tyr Gly Ser
                340                 345                 350

Leu Ala Ser Val Leu Ala Gln Tyr Ser Pro Gln His Leu Ala Gly Lys
                355                 360                 365

Arg Ile Gly Val Phe Ser Tyr Gly Ser Gly Leu Ala Ala Thr Leu Tyr
    370                 375                 380

Ser Leu Lys Val Thr Gln Asp Ala Thr Pro Gly Ser Ala Leu Asp Lys
385                 390                 395                 400

Ile Thr Ala Ser Leu Cys Asp Leu Lys Ser Arg Leu Asp Ser Arg Thr
                405                 410                 415

Gly Val Ala Gln Asp Val Phe Ala Glu Asn Met Lys Leu Arg Glu Asp
                420                 425                 430

Thr His His Leu Val Asn Tyr Ile Pro Gln Gly Ser Ile Asp Ser Leu
            435                 440                 445

Phe Glu Gly Thr Trp Tyr Leu Val Arg Val Asp Glu Lys His Arg Arg
    450                 455                 460

Thr Tyr Ala Arg Arg Pro Thr Pro Asn Asp Asp Thr Leu Asp Glu Gly
465                 470                 475                 480

Val Gly Leu Val His Ser Asn Ile Ala Thr Glu His Ile Pro Ser Pro
                485                 490                 495

Ala Lys Lys Val Pro Arg Leu Pro Ala Thr Ala Ala Glu Pro Glu Ala
                500                 505                 510

Ala Val Ile Ser Asn Gly
                515
```